United States Patent [19]

Berta

[11] Patent Number: 5,538,125
[45] Date of Patent: Jul. 23, 1996

[54] INDEXING AND FEEDING SYSTEMS FOR APPARATUS FOR GELATIN COATING TABLETS

[75] Inventor: Norbert I. Berta, Devon, Pa.

[73] Assignee: McNeil-PPC, Inc., Milltown, N.J.

[21] Appl. No.: 387,973

[22] Filed: Feb. 10, 1995

Related U.S. Application Data

[63] Continuation of Ser. No. 3,334, Jan. 12, 1993, abandoned, which is a continuation-in-part of Ser. No. 609,482, Nov. 5, 1990, Pat. No. 5,228,916.

[51] Int. Cl.⁶ .................................................. B65G 15/64
[52] U.S. Cl. ..................... 198/345.3; 198/740; 198/772; 198/465.1; 198/468.1; 198/418.1; 198/803.01
[58] Field of Search ..................... 221/301; 198/431, 198/740, 772, 345.3, 465.1, 465.2, 468.1, 418.6, 418.5, 803.01, 803.8, 803.11, 803.14, 803.15, 465.3, 448, 803.2, 418.2

[56] References Cited

U.S. PATENT DOCUMENTS

| | | | |
|---|---|---|---|
| 2,571,977 | 10/1951 | Warren | 198/418.2 |
| 2,847,809 | 8/1958 | Lindeman et al. | 198/418.5 X |
| 2,934,816 | 5/1960 | Van Nest et al. | 198/772 X |
| 3,106,282 | 10/1963 | Schmermund | 198/448 X |
| 3,228,513 | 1/1966 | Voullaire | 198/418.5 |
| 3,315,778 | 4/1967 | Kendall, Sr. et al. | 198/345.3 x |
| 3,811,548 | 5/1974 | Neff | 198/345.3 |
| 3,941,237 | 3/1976 | MacGregor, Jr. | 198/803.8 X |
| 4,041,674 | 8/1977 | Reid | 198/418.5 X |
| 4,114,752 | 9/1978 | Schiek | 198/431 X |
| 4,200,180 | 4/1980 | Dixon | 198/740 X |
| 4,222,166 | 9/1980 | Kurek et al. | 221/301 X |
| 4,462,517 | 7/1984 | Takata et al. | 221/301 X |
| 4,488,633 | 12/1984 | Kampf | 198/345.3 X |
| 4,516,673 | 5/1985 | Kashihara et al. | 198/740 X |
| 4,533,038 | 8/1985 | Richard | 198/803.8 X |
| 4,603,770 | 8/1986 | Hartness | 198/772 X |
| 4,693,370 | 9/1987 | Aceti | 198/803.15 X |
| 4,699,583 | 10/1987 | Grigoli et al. | 198/803.2 X |
| 4,792,033 | 12/1988 | Iwata et al. | 198/448 X |
| 4,820,524 | 4/1989 | Berta | 424/474 |
| 4,850,470 | 7/1989 | Ferkany | 198/740 X |
| 4,867,983 | 9/1989 | Berta | 424/451 |
| 4,921,108 | 5/1990 | Berta | 209/625 |
| 4,945,825 | 8/1990 | Florindez | 198/431 X |
| 4,965,089 | 10/1990 | Sauter | 477/3 |
| 4,966,771 | 10/1990 | Berta | 424/478 |
| 4,990,358 | 2/1991 | Berta | 427/3 |
| 5,097,935 | 3/1992 | Weiss | 198/465.3 X |
| 5,228,916 | 7/1993 | Berta . | |
| 5,234,099 | 8/1993 | Berta | 198/803.1 |
| 5,314,537 | 5/1994 | Berta | 118/30 |

FOREIGN PATENT DOCUMENTS

| | | |
|---|---|---|
| 0118856 | 9/1984 | European Pat. Off. . |
| 0194505 | 9/1986 | European Pat. Off. . |
| 0246693 | 11/1987 | European Pat. Off. . |
| 0448231 | 9/1991 | European Pat. Off. . |
| 2846565 | 7/1979 | Germany ............................ 198/740 |

*Primary Examiner*—D. Glenn Dayoan
*Attorney, Agent, or Firm*—Bernard F. Plantz

[57] ABSTRACT

Methods and apparatus for applying coating to products such as medicaments are disclosed. The present invention provides apparatus and methods for controlling the loading and feeding of tablets onto carrier plates for transfer to various processing stations of the coating system. A novel plate indexing apparatus includes a box cam follower device mounted to an engagement bar for incrementally advancing the plates in a precisely controlled manner. A second complementary shaped engagement bar provides a locking mechanism to ensure the plates are always under positive control. In one embodiment the plate indexing apparatus also controls the feeding of the tablets. An alternative embodiment includes a vacuum pick-up system for feeding tablets onto the carrier plates as the plates are incrementally advanced.

33 Claims, 13 Drawing Sheets

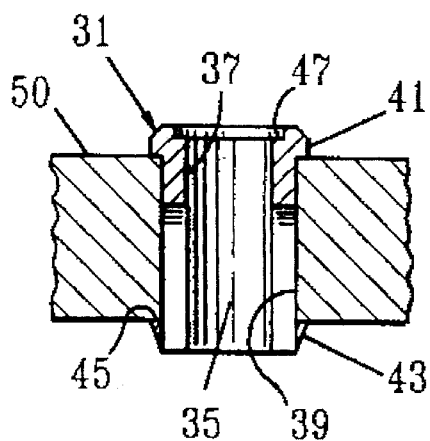
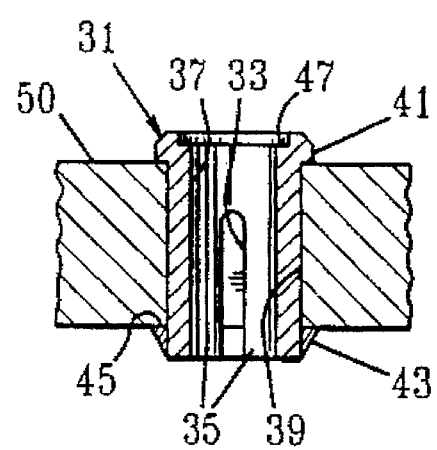
FIG. 7A        FIG. 7B
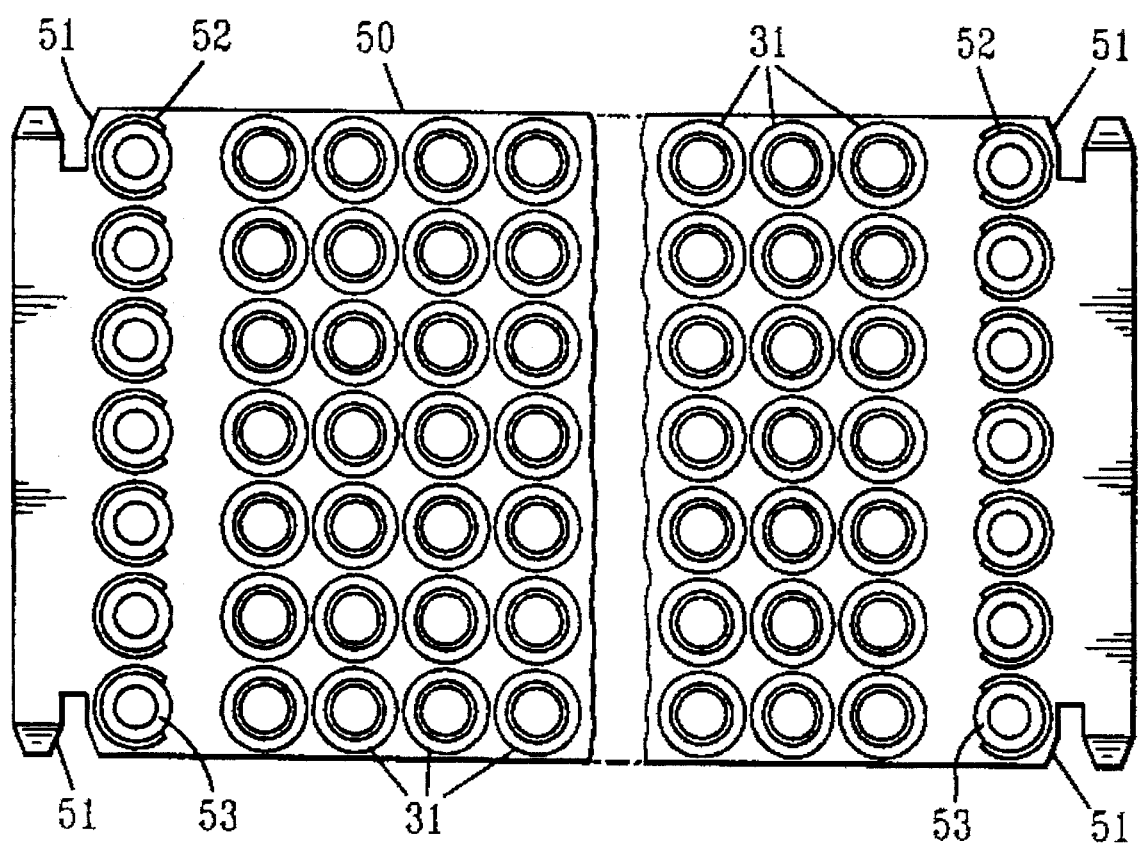
FIG. 8

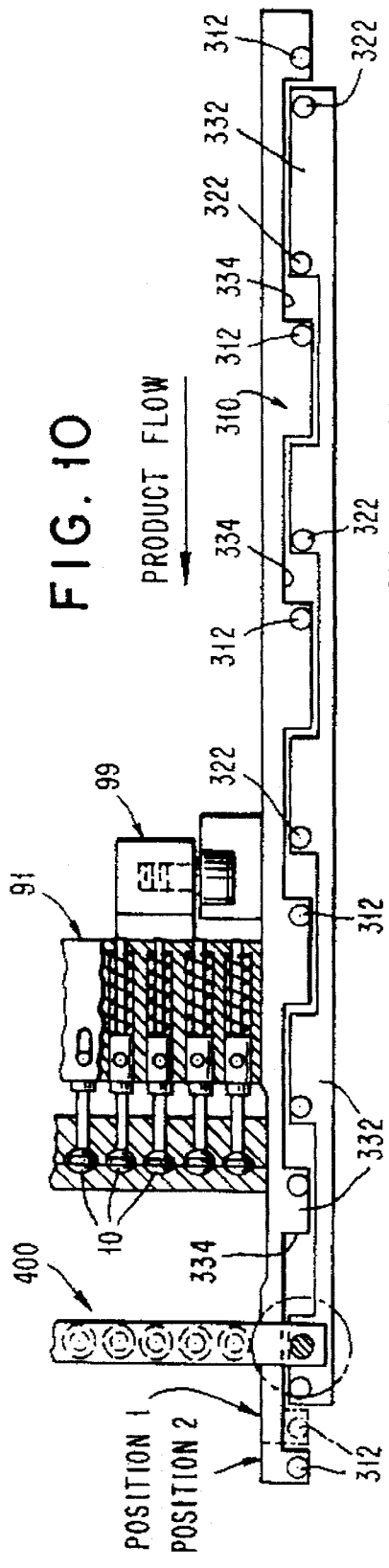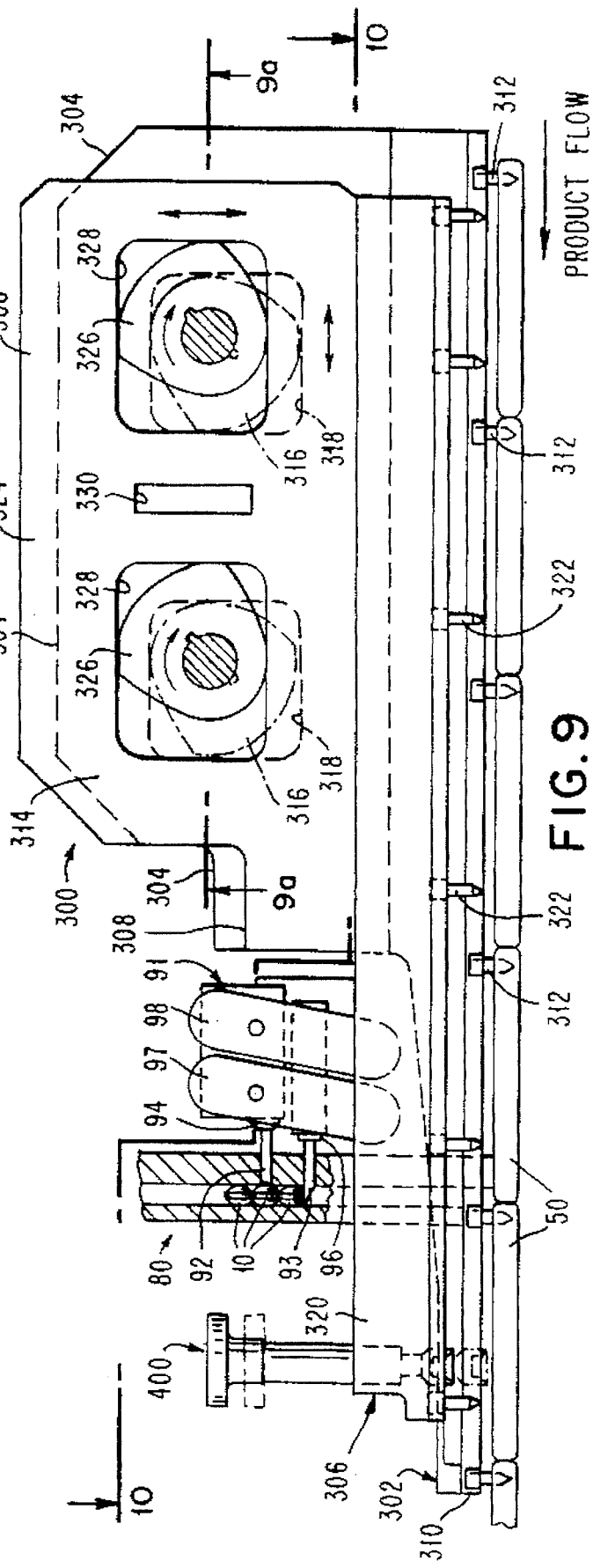

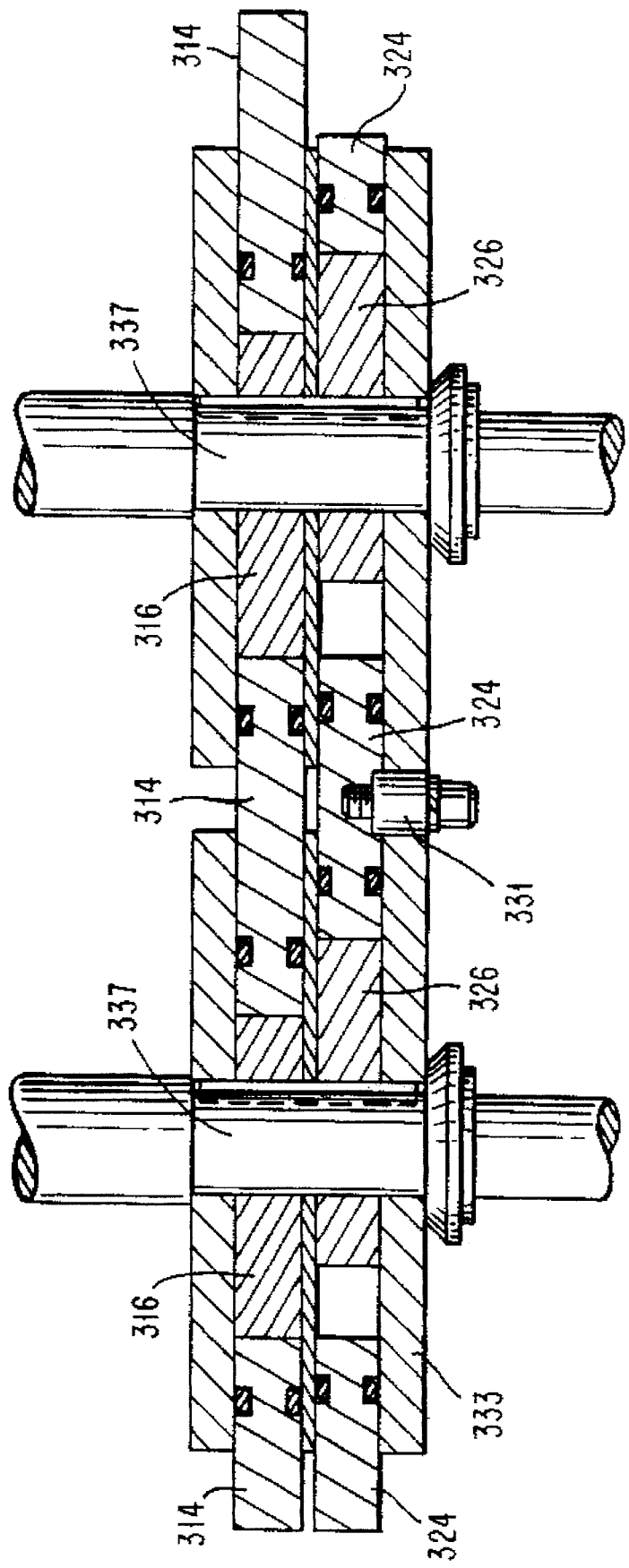

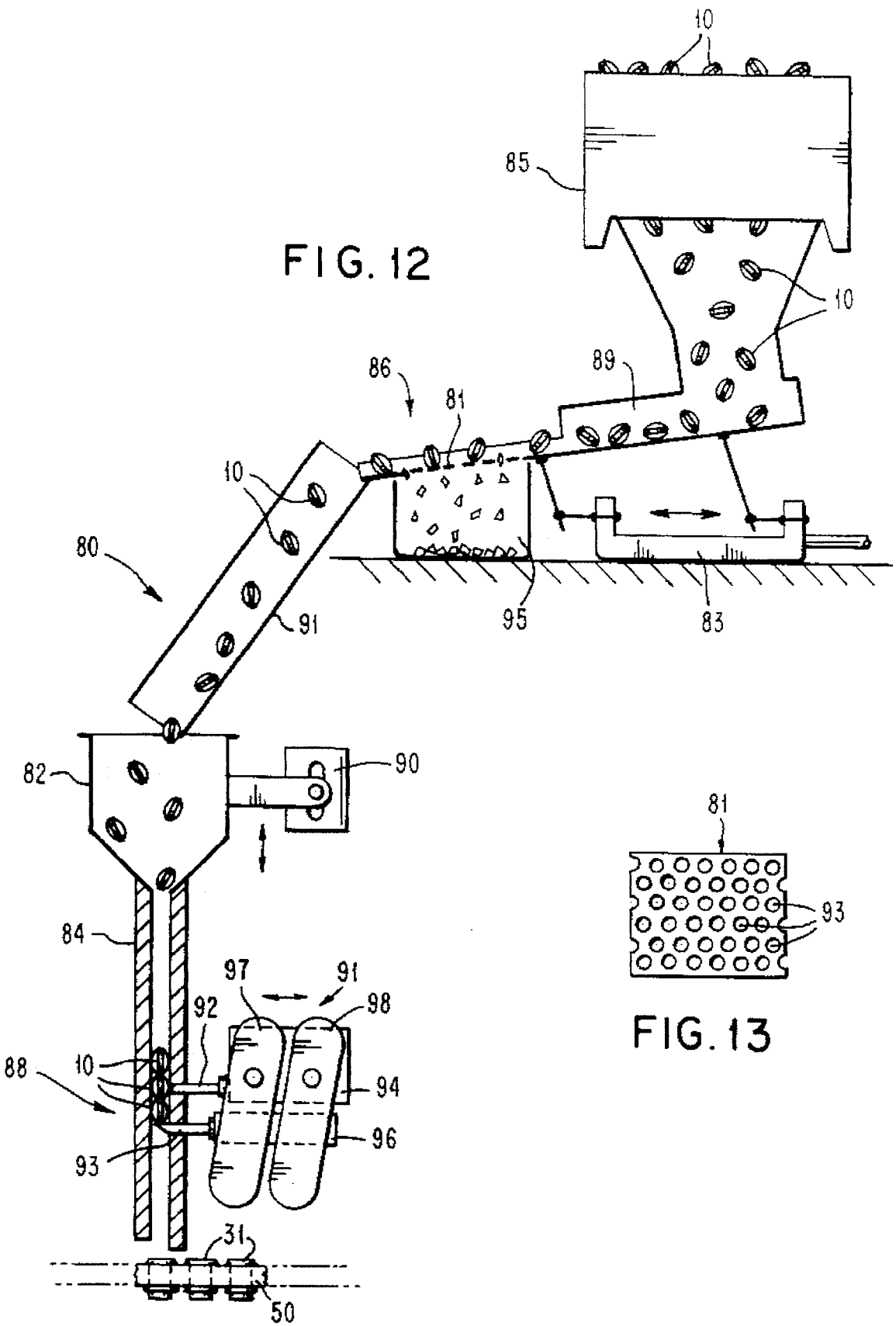

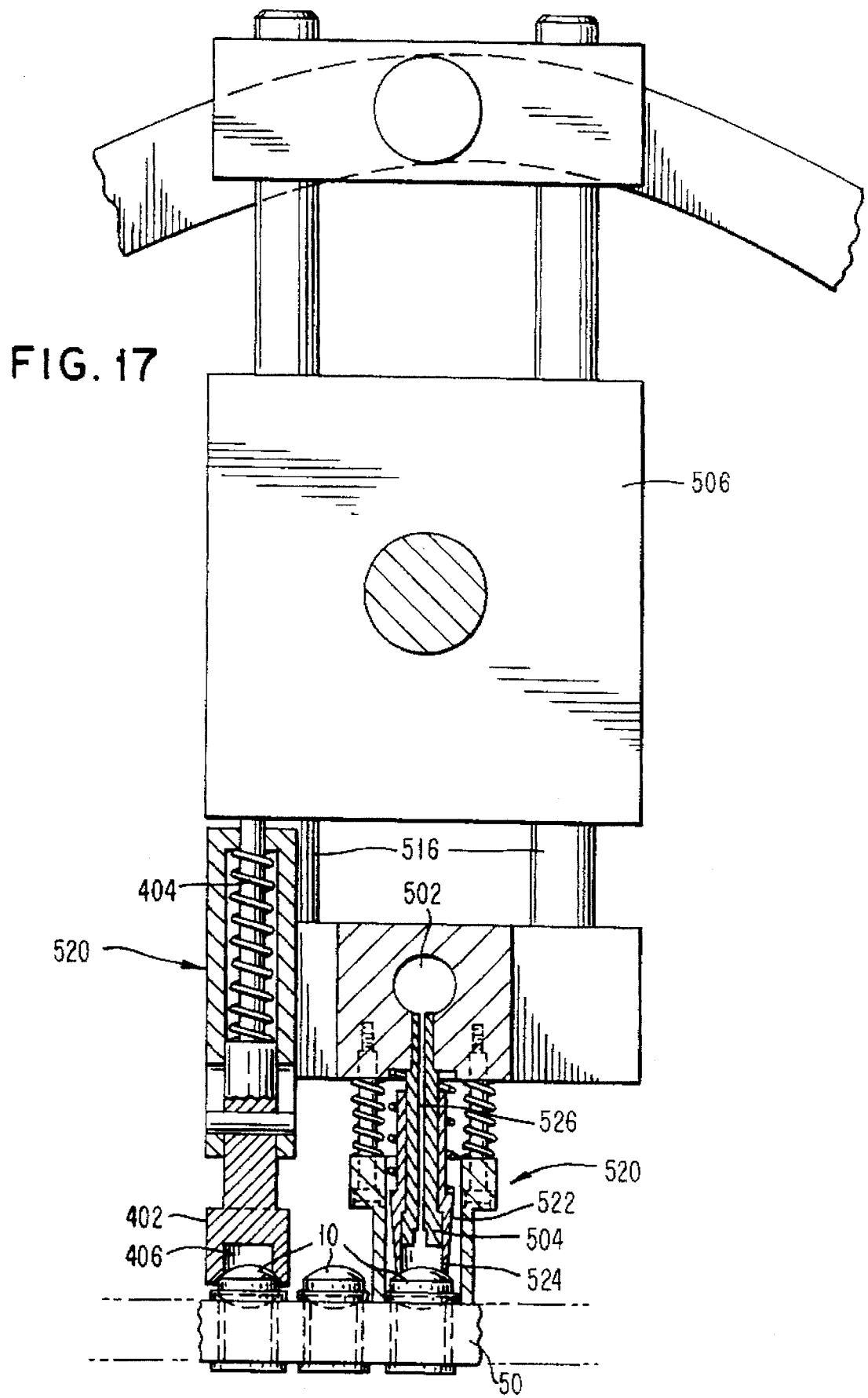

INDEXING AND FEEDING SYSTEMS FOR APPARATUS FOR GELATIN COATING TABLETS

This is a continuation of application Ser. No. 08/003,334, filed Jan. 12, 1993 now abandoned, which is a continuation-in-part of application Ser. No. 07/609,482, filed Nov. 5, 1990, now U.S. Pat. No. 5,228,916.

The present invention relates to methods and apparatus for forming a coating on a product and, more particularly, to methods and apparatus for forming a coating comprised of a gelatinous substance on a tablet. The present invention further relates to methods and apparatus for loading tablets into the coating apparatus for processing.

The present invention is related to my prior U.S. Pat. No. 4,921,108 issued on May 1, 1990; U.S. Pat. No. 4,867,983 issued on Sep. 19, 1989; U.S. Pat. No. 4,820,524 issued on Apr. 11, 1989 and U.S. Pat. No. 4,966,771 issued on Oct. 30, 1990, and my U.S. patent application Ser. No. 483,154, filed Feb. 22, 1990, now U.S. Pat. No. 5,234,099, which are assigned to the assignee of the present application and incorporated by reference as if fully set forth herein.

The present invention is also related to my U.S. patent application Ser. Nos. 08/003,158, 08/003,547, 08/003,348 and 08/003,349 all filed concurrently herewith, which are all assigned to the assignee of the present application and incorporated by reference as if fully set forth herein.

BACKGROUND OF THE INVENTION

Many products, from prescription drugs to commonly available vitamin tablets to candy, are manufactured in a form which may be described as a "tablet." The primary function of a tablet is to provide a single dose or "serving" of the product in a manner which is convenient to manufacture, package and consume. As pointed out in my previous patents and applications, referenced above, it has been found that certain individuals suffer from physiological and psychological problems which impede their ability to swallow tablets. It has also been found that by providing tablets with a smooth coating, such as a coating comprised of gelatin or a gelatinous substance that the "swallowability" of a tablet is greatly enhanced. Such coatings and the general considerations involved in their application, such as preparation and drying time, are well known to those of ordinary skill.

In addition to enhanced swallowability, there are numerous other reasons that it is desirable to provide a coating on a tablet. Such coatings protect the underlying product from deterioration and also serve to permit identifying colors or markings to be incorporated onto the design of the product, promoting product differentiation and brand identification. As pointed out in my previous patents and applications, it is also desirable in some instances to overlap two or more coatings to form a seam, thereby simulating the appearance of a hard gelatin capsule while providing a coated, solid (and thus tamper resistant) product.

Methods and apparatus for applying a gelatinous coating or other coating to a product which is in the form of a tablet are well known to those of ordinary skill. Such methods may include pan dipping or vacuum spraying of the coating material on to the tablet. Such methods are crude, however, producing uneven coatings which are generally unacceptable for commercial use. In an effort to improve the state of the art, the inventions disclosed by my previous patents and applications have provided methods and apparatus whereby individual products are held partially within a sleeve or "collet" and the exposed portion of the product precisely lowered into a dipping tank. As disclosed, bars or plates containing a plurality of product to be dipped are conveyed and rotated and the product itself is manipulated to provide even coatings of high quality and consistency at high volume. These inventions, however, do not permit every type of product such as certain styles of tablets and medicaments to be coated—or at least to be coated in a particular manner. For example, dipping the circular face of a substantially cylindrical tablet whose height is relatively small compared to its diameter would be difficult using the apparatus disclosed by my prior patents and applications, particularly if a circumferential seam is desired. Other examples include the difficulty of coating either a fragile product or applying fragile coating compositions. It has been found that certain coatings will be marred by the friction fit within the collets or similar retaining devices making these unsuitable for use in the apparatus of my prior inventions.

It is known to transport individual tablets or capsules through an immersion coating bath by retaining the tablets on individual vacuum tubes. For example, Banker U.S. Pat. No. 3,896,762 discloses a rotary coating apparatus for pharmaceutical solid dosage forms. Since the surface of the coating is horizontal it is tangential to the path of the tablet; accordingly, Banker discloses that it is necessary to rotate the vacuum tube holding the tablet around its longitudinal axis to achieve an even coating. There are, however, a number of practical shortcomings in the apparatus disclosed. First, although a dryer and ejector are disclosed, the overall system does not lend itself to high volume production or provide for modifications in drying time or inspection, etc. Secondly, the system disclosed by Banker is directed to passing one-half or more of the total depth dimension of the tablet through the coating solution. The tablet is then randomly ejected, with no provision being made to align or otherwise control the orientation of the tablet and the uncoated portion, if any, which exists. Moreover, there is no provision for adjusting the coating to achieve multi-colored or capsule-like coated products. Therefore, one of ordinary skill will appreciate that the system disclosed by Banker is of limited use in current manufacturing environments, where high volume and flexibility are important, along with the need for consistency and high quality.

Therefore, there exists a need for methods and apparatus which can consistently place a precisely defined amount of coating material on an individual product. Such methods and apparatus should be capable of producing coated products at high volume and should possess inherent flexibility to permit new designs and types of coatings to be incorporated without an undue degree of retooling. Moreover, it is extremely important that the products be introduced into the system in a highly controlled manner to enable the coatings to be accurately applied.

SUMMARY OF THE INVENTION

The present invention provides novel product loading apparatus and methods for precisely controlling the insertion of solid tablet medicaments onto carrier plates for transfer to various processing stations for coating the tablets with gelatin. The invention includes an indexing means for incrementally advancing a plurality of product carrier plates through a feeder device. The plate indexing means also includes means for ensuring that the carrier plates are always under positive control throughout the advancement procedure. In one embodiment a box cam mechanism moves a first plate engagement bar in four directions to advance the carrier plates and a two-way cam mechanism moves a second plate engagement bar in two directions to alternately lock and unlock the plates. The plate indexing means is connected to the feeder device in order to coordinate the loading of tablets onto holders in the carrier plates in cooperation with the advancement of the plates. A setting pin is connected to the plate indexing means to properly seat the loaded tablets in their individual holders prior to advancing to other processing stations. In one embodiment, a passive loading mechanism is described in which tablets are loaded onto the holders by the movement of the carrier plates. In another embodiment, the tablets are loaded using a rotatable vacuum pick-up head system for picking up tablets from the feeder device and placing them onto the product holders. The feeder device is also provided with selection means for sifting out partial tablet pieces. The precise indexing of the product carrier plates and the loading and setting of the tablets onto tile plates in accordance with the present invention greatly increases the efficiency of the gelatin coating processing system resulting in greater productivity and lower costs.

BRIEF DESCRIPTION OF THE DRAWINGS

FIGS. 7a and 7b are cross-sectional views of another embodiment of a tablet holder of the present invention.

FIG. 8 is a plan view of a product carrier plate of one embodiment of the present invention.

FIG. 9 is a partial elevational view of the plate indexing means of the present invention.

FIG. 9a is a cross-sectional view taken along lines 9—9 of FIG. 9.

FIG. 10 is a cross-sectional view taken along lines 10—10 of FIG. 9.

FIG. 12 is a diagrammatic representation of the feeder means of the present invention.

FIG. 13 is a diagrammatic representation of a perforated plate of a separation means of one embodiment of the feeder means of the present invention.

FIG. 17 is a cross-sectional view of another embodiment of the dispensing means of FIG. 16 with a setting means attached thereto.

DETAILED DESCRIPTION OF THE PREFERRED EMBODIMENTS

Figure 1:
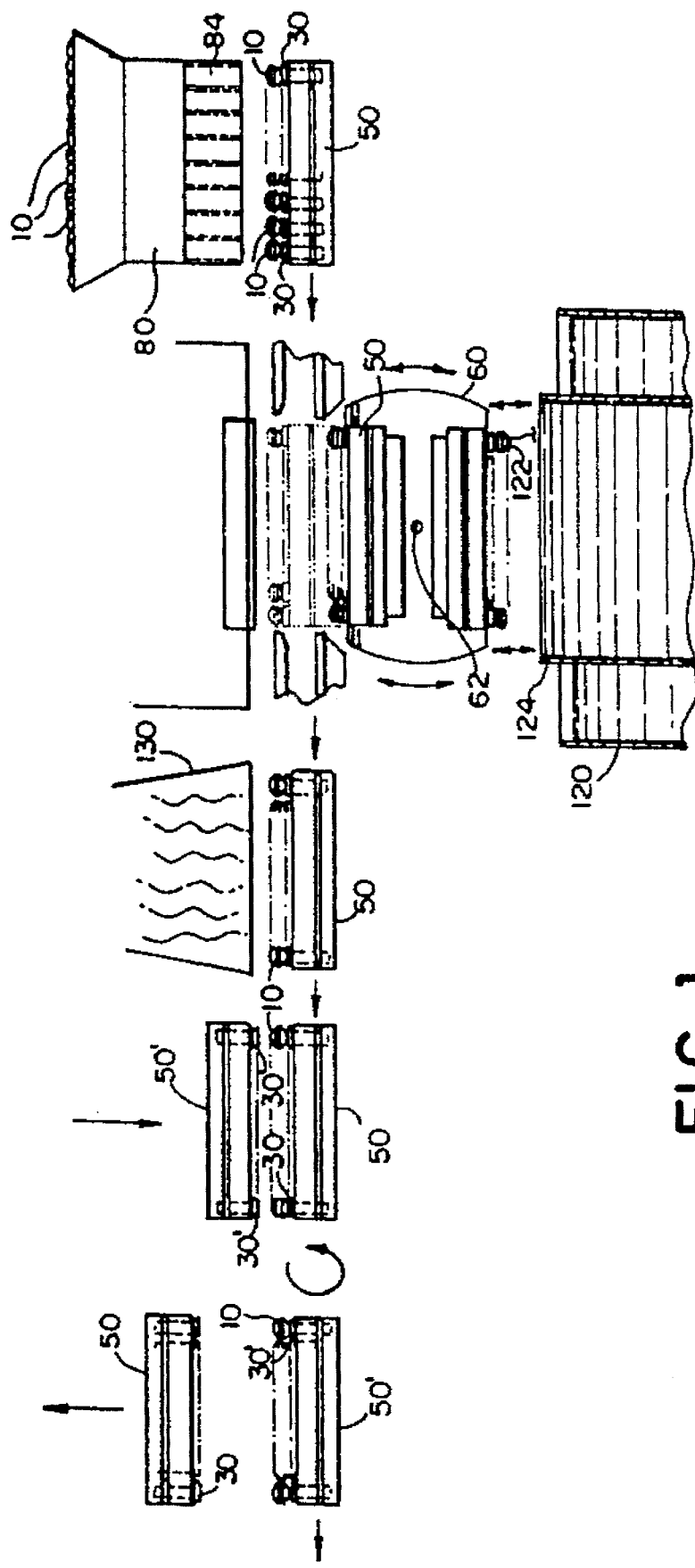
FIG. 1 is a partially diagrammatic, partially schematic representation of the coating apparatus of the present invention.

A generalized representation of the apparatus used in a preferred embodiment of the present invention is shown in FIG. 1. It will be understood that the descriptions set forth may be applied to numerous types and shapes of products. The type of tablet illustrated and the sequence shown are for purposes of explanation only.

A plurality of the product 10 to be coated is placed in a feeder means 80. Preferably, the feeder will be comprised of a hopper 82 and a series of feeder tubes 84 which align, orient and dispense the product 10 in the appropriate manner. Initially disposed directly beneath the feeder tubes 84 and in registration therewith is a plate 50. The plate 50 has a plurality of tablet holders 30 which, as explained below, restrain the product during certain portions of the coating process. The tablet holders 30 preferably correspond to the feeder tubes 84 and thus, most preferably, each tube 84 feeds a single product 10 into a single tablet holder 30.

Conveyor means transfer the plate 50 from the feeder 80 to the vacuum chamber 60. In a preferred embodiment shown in FIG. 1, the vacuum chamber 60 is adapted to receive and make vacuum tight connections with two plates 50. As shown by the arrows, the vacuum chamber 60 is further provided with manipulating means whereby it may be moved up and down, and rotated about a pivot point 62.

A first dipping tank 120 is disposed beneath the vacuum chamber 60 and is filled with a quantity of coating material. Preferably a coating material such as gelatin is used and, most preferably, the dipping tank 120 is provided with pumps and conduits whereby the coating material is continuously circulated. As illustrated, the dipping tank is most preferably constructed to form a meniscus surface 122 by pumping the coating material into an inner tank 124 which is permitted to overflow into the larger tank 120. Such a system prevents the coating material from hardening while the apparatus is in use and helps to ensure that the coating material presents the same even and substantially level surface to the product being dipped at all times.

In operation, the plate 50 is moved into engagement with the vacuum chamber 60 and then the chamber 60 and the plate 50 are rotated one-half revolution. As explained below, the vacuum chamber 60 creates a vacuum within the tablet holders 30 which holds the product 10 in place and in the correct orientation to be dipped. The vacuum chamber 60 is next lowered into dip tank 120 to a predetermined depth and then withdrawn. The vacuum chamber 60 is then rotated one and one-half revolutions in order to return the plate 50 to its original orientation. The additional full revolution beyond that required provides a dwell time, permitting the coating to initially "set" and also prevents the coating from running or sagging due to gravity by constantly reorienting the product 10. However, a rotation of as little as one-half of a revolution may be adequate in some instances. At this point, the plate 50 may be returned to the conveyor means and removed from the vacuum chamber 60.

The design of the vacuum chamber 60 and placement of the dip tank 120 illustrated permit a wide variety of coatings to be effectively and efficiently achieved. Although the dipping of a substantially cylindrical tablet having concave faces to form a coating having circumferential seam is illustrated, those of ordinary skill will understand that numerous other shapes of product, as well as other coating schemes are possible using the apparatus disclosed. As will be explained below, the shape of the tablet holders 30 and the design of the sub-components of the vacuum chamber 60 may be readily adapted for particular requirements. Also, as illustrated in FIG. 1, throughput may be increased by designing the vacuum chamber 60 to form a vacuum tight seal with further plates 50, such that each time the vacuum chamber 60 is rotated, a plate 50 which has already been lowered into the dipping tank 120 is returned to the conveyor means.

After the plate 50 containing the partially coated product 10 is removed from the vacuum chamber 60 the plate may be passed through a dryer means 130 for curing the coating material. As will be understood by those of ordinary skill, the dryer 130 will be chosen to correspond to the heat and moisture requirements of the coating material being used. Radiant heat, forced hot air, microwave dryers and combinations of these types are among the types available. Depending upon the type of dryer 130 chosen, one or more conveyors and other apparatus may be required to transfer the plates 50 into and out of the dryer 130.

After the coating has been cured, the plate 50 is again returned to conveyor means and is preferably transferred to another location. At this point, although only a portion of each individual product 10 has been coated, it may be desirable to eject the product 10 and consider the process complete. This may be true, for example, where the product has already been coated and the above-described process is carried out to add a second color to a portion of the product.

In a preferred embodiment, however, the present invention provides methods and apparatus which permit the uncoated portion of the product 10 to be coated. First, a second plate 50' is positioned in registration with the product contained on the first plate 50, as illustrated in FIG. 1. The second plate 50' is lowered until the coated side of the product 10 is disposed within the tablet holders 30' of the second plate 50'. The resulting "sandwich" of the first plate 50, the product 10 and the second plate 50' is then rotated one-half revolution by the conveyor/manipulator means. As shown, the positions of the plates 50,50' are thus reversed, and when the first plate 50 is removed the uncoated portion of the product 10 is exposed. The second plate 50' may then be transferred to the starting point of the dipping process and put through the sequence of manipulations necessary to form a coating which were set forth above using either the same apparatus or further apparatus, using either the same coating material or a different coating material.

In the instance where the same apparatus is used to place coating upon the uncoated portion of the product 10, the second plate 50' may be preferably conveyed or otherwise transported to a location just before the vacuum chamber 60, i.e., between the vacuum chamber 60 and the feeder 80 illustrated in FIG. 1. The second plate 50' would simply be inserted into engagement with the vacuum chamber 60 and the above described apparatus would carry out substantially the same sequence of functions in terms of dipping the product 10, curing the coating as needed, etc. After the product 10 has been fully coated and cured, it may be ejected prior to the transfer stage between the first and second plates 50,50'.

In another embodiment of the present invention, after the partially coated product has been transferred to the second plate 50', the plate 50' may enter a duplicate series of apparatus, such as that described above with reference to FIG. 1. In other words, a second vacuum chamber, dipping tank, dryer, and manipulating and conveying apparatus may be provided. After the product 10 is coated and cured using this second set of apparatus, the completed product is ejected.

Figure 2:
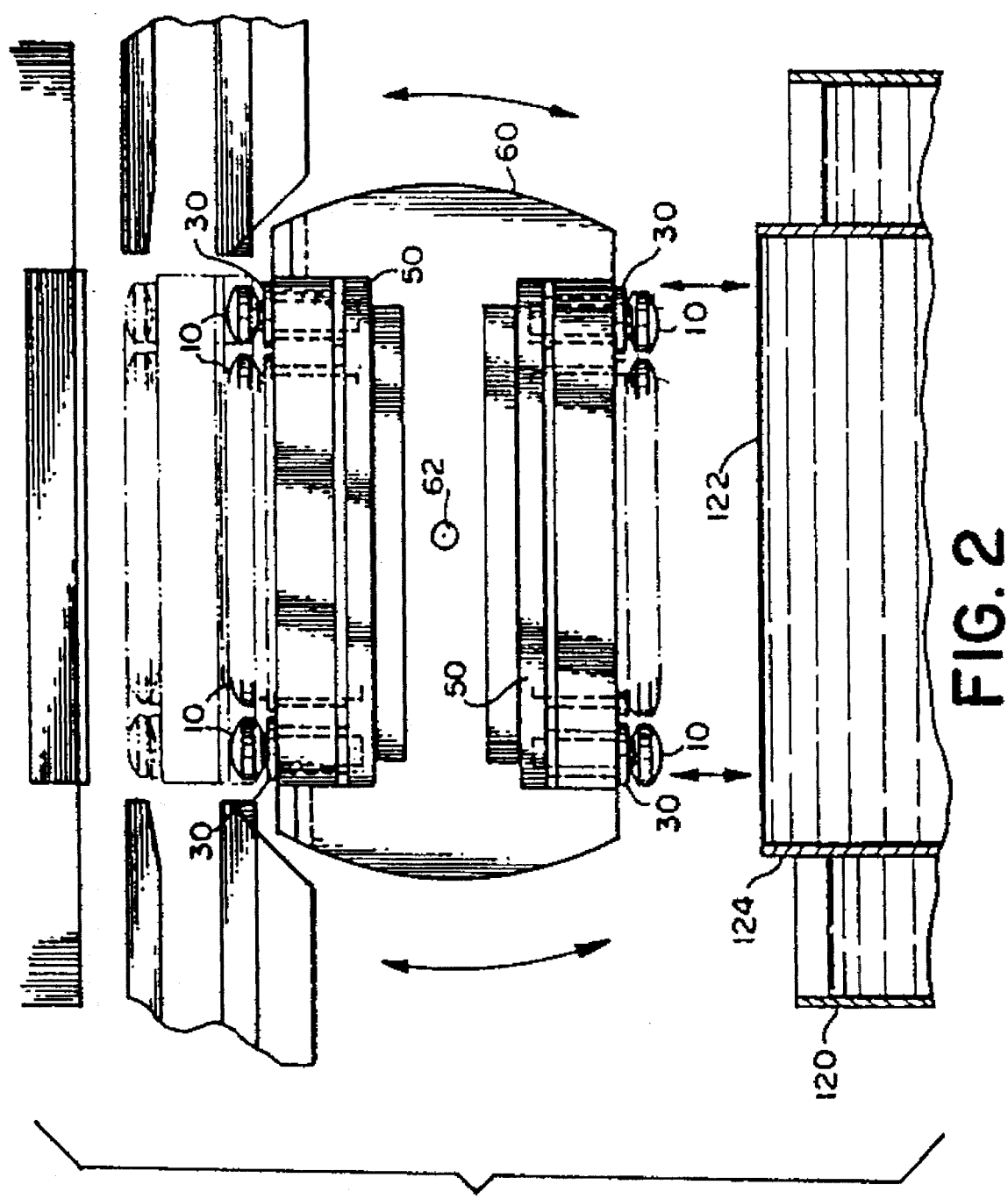
FIG. 2 is a broken away, partially cross-sectioned side view of a portion of the apparatus of FIG. 1.

Referring now to FIG. 2, a more detailed view of the vacuum chamber 60 described above is shown. As explained above, in a preferred embodiment two plates 50 (or 50') are retained in a vacuum tight seal upon the vacuum chamber 60, thereby permitting more efficient indexing between the raising and lowering of the apparatus and the infeed and outfeed of the plates 50 from the vacuum chamber 60.

As shown, the entire chamber may be raised or lowered to bring the product 10 into contact with the surface of the coating material 122. The vertical motion also preferably provides a transfer between the vacuum chamber 60 and the conveyor means, as shown in phantom in FIG. 2. This latter vertical movement also provides clearance when the vacuum chamber 60 is rotated during the dipping process explained above with reference to FIG. 1.

Figure 3:
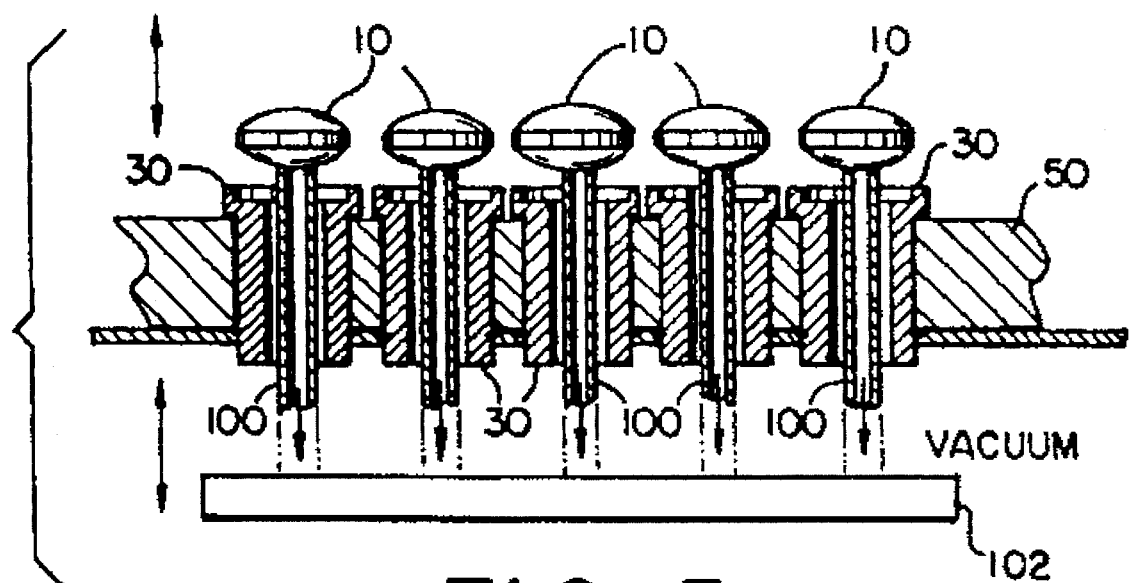
FIG. 3 depicts a cross-sectional view of the tablet holders and plate used in one embodiment of the present invention.

Further details of the vacuum chamber 60 are shown in FIG. 3, which illustrates broken-away section of the plate 50 and the vacuum chamber 60. As seen in cross-section, the plate 50 has a plurality of tablet holders 30 inserted into a series of openings. The plate 50 rests upon the vacuum chamber 60 and forms a seal therewith. A plurality of vacuum tubes 100 extend through the tablet holders 30 and, when in use, engage and slightly lift the product 10 from the tablet holders 30 as shown. The vacuum created within the vacuum chamber 60 is channeled through the vacuum tubes 100 by a manifold or similar means, thereby permitting the vacuum to act upon the surface of the product 10 when contacted by the vacuum tubes 100. By providing vacuum tube actuator means 102 for raising and lowering the vacuum tubes 100 relative to the vacuum chamber 60, the vacuum tubes may be selectively placed in the raised position illustrated. The actuator 102 may be a common bar or mounting structure which is moved by a gear, cam or pulley system.

When in the position illustrated, it is possible to invert or otherwise manipulate the product 10 as described above without friction or the use or mechanically actuated clamps. The vacuum handling system disclosed by the present invention provides a secure retention of the product while minimizing the possibility of damaging either the coating or the product 10 itself. As explained above, the methods and apparatus of the present invention are useful for numerous shapes and sizes of product 10, however, most preferably, the product 10 will have one or more curved surfaces, as illustrated. The curved surfaces permit the tubes 100 to be made from a rigid material such as stainless steel. Those of ordinary skill will realize however, that nearly any shape and any orientation of product may be retained using appropriately designed vacuum tubes. Finally, in certain instances it will be desirable to provide a cushion or resilient tip on the distal end of the vacuum tube in order to ensure a sufficient grip.

Figure 4:
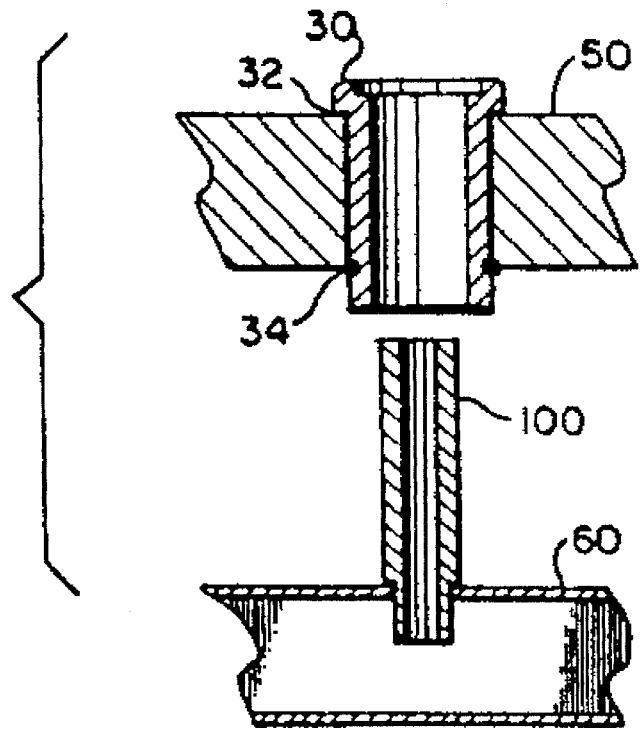
FIG. 4 is a broken away cross-sectional view of the plate of FIG. 3, illustrating the tablet holder and vacuum tube used in one embodiment of the present invention.

Referring now to FIG. 4, one embodiment of the tablet holder 30 is illustrated. A shoulder 32 is formed at a first end of the tablet holder to provide a positive stop. A groove is formed at a second end, into which an "O" ring or the like may be engaged to retain the tablet holder 30 in the plate 50. As will be understood by those of ordinary skill, the tablet holder 30 and the plate 50 may be in certain instances formed as an integral component. FIG. 4 also illustrates the vacuum tube 100 in the withdrawn position. When the vacuum tube 100 is in the withdrawn position, the depression formed in the tablet holder 30 is the only means for restraining the product 10 (not shown in FIG. 4).

FIGS. 7a and 7b show a second embodiment of the tablet holder for use in plates 50. Tablet holder 31 shown in FIGS. 7a and 7b is provided with a plurality of slots 33 forming resilient fingers 35. FIG. 7a is a cross-section taken through the slots 33, and FIG. 7b is a cross-section taken with the holder 31 rotated 90° from its position in FIG. 7a. In the embodiment shown in FIGS. 7a and 7b, a pair of slots 33 are provided thereby forming a pair of resilient fingers 35. Slots 33 are disposed longitudinally through the walls of holder 31. Holder 31 is generally in the form of a cylinder having a central bore 37. Tablet holder 31 is retained in the opening 39 of plate 50 by shoulder portion 41 on one end and angled flange 43 on a second end. For ease in installation the size of upper surface 45 of angled flange 43 may be significantly reduced at the portion of the side walls located immediately adjacent to slots 33 as shown in FIG. 7a. The flange 43 may gradually increase to its largest surface area located 90° from slots 33 as shown in FIG. 7b. The holder 31 is also provided with seat 47 for accepting a tablet therein. It will be understood by those of ordinary skill that the seat 45 may be shaped appropriately to match the shape of the product being held.

The holder 31 is a "push-in" holder that does not require o-rings or the like that are susceptible to wear and tear. In order for the holder 31 to be secured in the plate 50, the outer diameter of the annular resilient fingers 35 forming the cylinder of holder 31 must be slightly larger than the diameter of the opening 39 in plate 50. The angle of flange 43 enables the holder 31 to be inserted through the opening 39 and to cause the fingers 35 to be slightly compressed toward each other as the holder is passed through the plate 50. When the flange 43 clears the opening 39 and plate 50, the resilient fingers 35 spring back to their original position causing flange 43 to engage plate 50 thereby securing the holder 31 therein.

FIG. 8 shows a plan view of a carrier plate 50 for retaining the plurality of product holders 30 or 31. The carrier plate 50 of FIG. 8 includes a plurality of longitudinal rows of individual product holders 31. The plates 50 are preferably from 4 to 5 inches wide and approximately one-half to one inch thick. In one embodiment, the plate 50 is made about 23 to 24 inches in length enabling the plate to include 7 rows each containing 33 holders for a total of 231 holders.

A preferred embodiment of the carrier plate 50 of the present invention is machined from tool plate aluminum. It is also preferred that the aluminum have a protective coating such as an anodized coating applied to the surface. The plate 50 is rectangular and symmetrical, having four easily spaced slots 51 disposed near the four corners which engage the conveyor and/or holding means. Also provided at either end are alignment and transport holes 52 which contain retaining bushings 53 which are used to manipulate the plate 50 as it is advanced through the feeder means 80 and through other processing stations.

The present invention also provides methods for coating a product 10 in accordance with the present invention. A preferred embodiment of the methods of the present invention is illustrated by the sequence of views in FIG. 5. For purposes of illustration and explanation a single product 10, vacuum tube 100 and tablet holder 30 are illustrated, along with broken away portions of other apparatus such as the plate 50. As shown in the upper left section of FIG. 1, a plate 50 containing a tablet holder 30 is positioned beneath the feeder means 80 for feeding a tablet described above and a product 10 is disposed within the tablet holder 30. Next, the plate 50 containing the individual products 10 is moved into the vicinity of the vacuum chamber 60, where it is cleaned of dust and particulate matter. For clarity, the representation of the vacuum chamber 60 is omitted from the other views shown in FIG. 5. An individual vacuum tube 100 is then brought into position and placed in close proximity or contact with the product 10. At this point, the vacuum created within the vacuum tube 100 "picks up" or engages the product 10. After the individual products 10 have been engaged by the vacuum tubes 100, the entire plate 50 is rotated one-half of a revolution, suspending the product 10 by the vacuum tube 100. The vacuum tube 100 and the product 10 attached thereto may now be moved into position and lowered into a coating tank 120. The depth to which the product 10 is lowered is a function of the motion of the vacuum tubes 100 and plate 50, which may be precisely regulated by hydraulic actuators, gear trains or other means for actuating the vacuum tube 100 and/or moving the plate 50. The vacuum tube 100 and the partially coated product 10 are then withdrawn from the coating tank 120, but the product 10 is not fully withdrawn into its holder 30. Instead, the plate 50 and partially extended vacuum tubes 100 are rotated one and one-half revolutions, returning the plate 50 to its initial orientation. The additional revolution provides a dwell, permitting the coating to initially set, as well as aiding in the provided evenness of the coating by preventing the coating from running due to gravity. In certain embodiments, however, this dwell may be unnecessary and the plate need only be rotated one-half of a revolution. After the plate 50 has been returned to its initial position, the vacuum tube 100 may be withdrawn until the product 10 again rests in a holder 30 within the plate 50. Once the vacuum tube 100 has been sufficiently withdrawn, the vacuum connection to the product 10 is broken and gravity and the holder 30 restrain the product 10.

Figure 5:
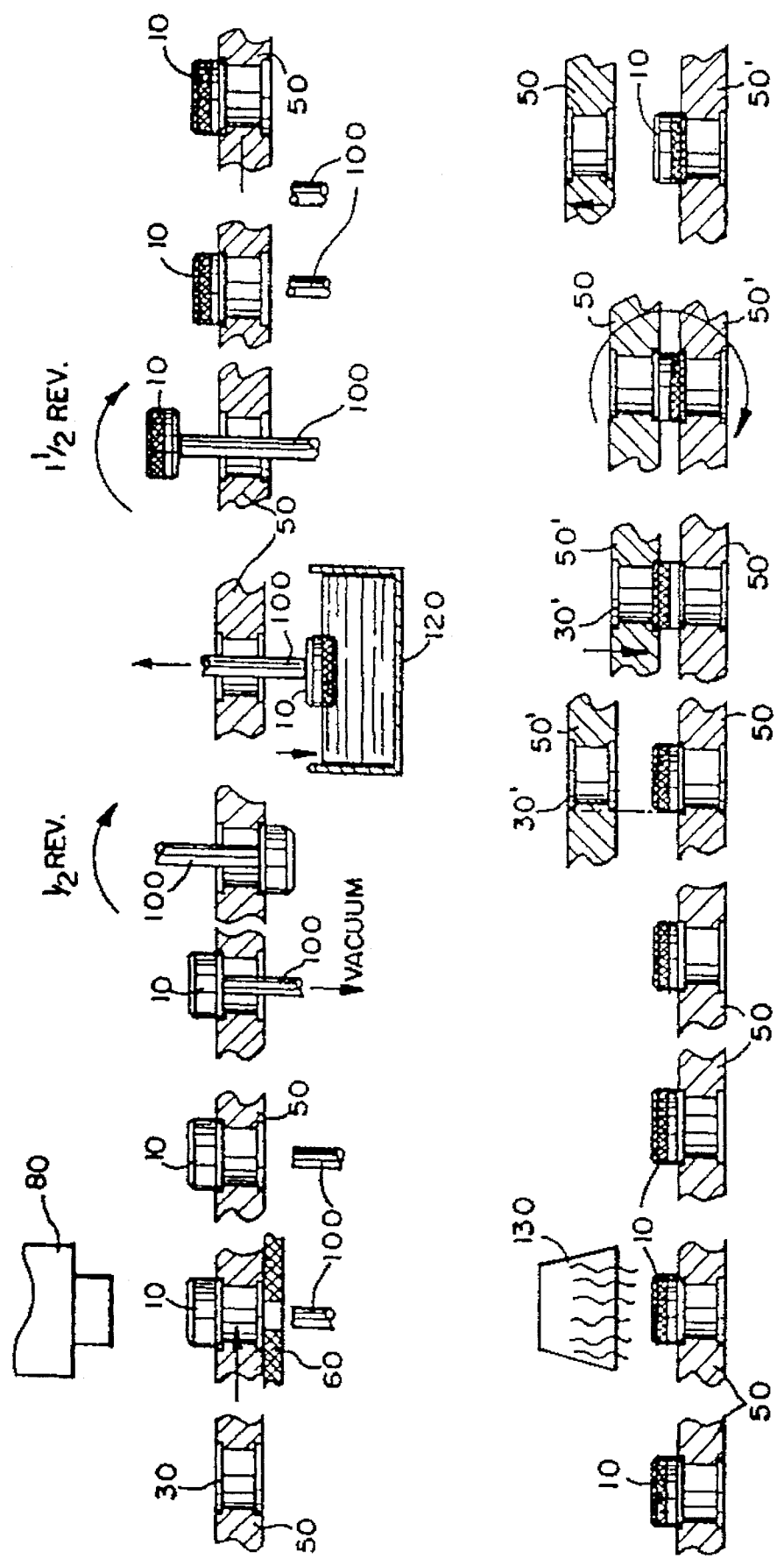
FIG. 5 is a partially diagrammatic, partially schematic representation of the steps of a preferred method for coating a tablet in accordance with the present invention.

As shown at the lower left portion of FIG. 5, once the individual products 10 have been released from the effect of the vacuum, the plate 50 bearing the partially coated individual products 10 may be moved into a dryer 130. Using conveyors or other conventional means, the plates are pushed into the dryer 130 and dried. After the coating has cured and the plates 50 have exited the dryer 130, a second plate 50' is moved into position such that the tablet holders 30' in the second plate 50' are in registry with the tablet holders 30 in the first plate 50, which contain the partially coated product 10. The second plate 50' is lowered toward the first plate 50 until the tablet holders 30' in the second plate 50' have engaged the product held in the first plate 50. Thus, as illustrated, the product 10 is "sandwiched" between the first and second plates 50,50'. The pair of plates 50,50' are then rotated one-half revolution, thereby reversing the relative positions of the first and second plates 50,50'. The first plate 50 is then raised, leaving the uncoated portion of the product 10 on the top, exposed, and the coated side on the bottom, i.e., within the tablet holder 30 of the plate 50'.

At this point, the preferred embodiment of the method illustrated has completely coated and cured a coating on about one-half of the product 10. It will be understood, however, that the above-described method may be repeated by transferring the plate 50' shown in the lower right section of the illustration to the upper left section, in other words, to the beginning of the process at the point immediately after the individual products 10 have been loaded into the plates 50. In this embodiment of the present invention, the above-described process is repeated and the remainder of the product 10 is coated. It should be further understood, however, that in any event, more or less than one-half of the tablet may be coated to provide different overall coating effects. For instance, if both "passes" coated less than one-half the height of the tablet, a band of uncoated product would remain exposed. On the other hand, if one or both of the "passes" were carried out to a depth substantially greater than one-half the height of the tablet, in overlapped "seam" appearance would be created.

Figure 6:
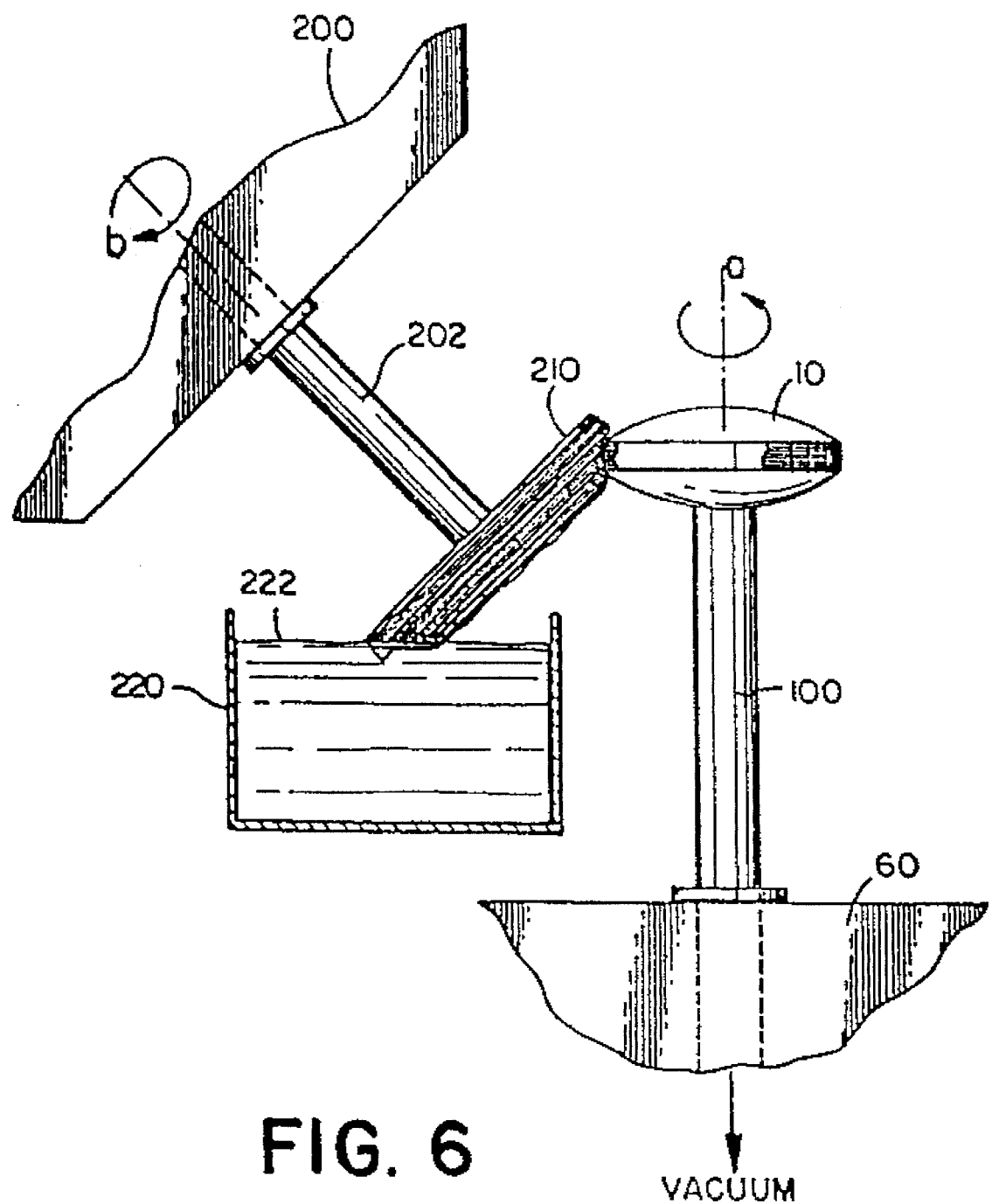
FIG. 6 is a broken away cross-sectional view of a portion of another embodiment of the present invention in which a band of coating material is applied to the products.
Figure 11A:
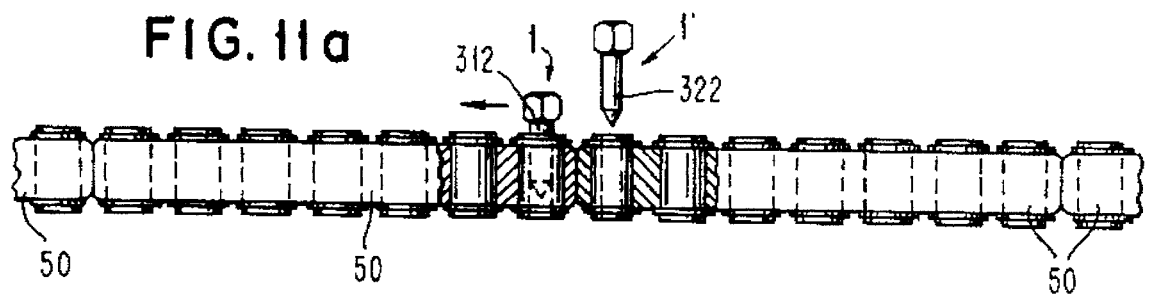
FIGS. 11a–11e are a schematic representation of the sequential movement of the engagement bars of the indexing means of FIG. 9.
Figure 11B:
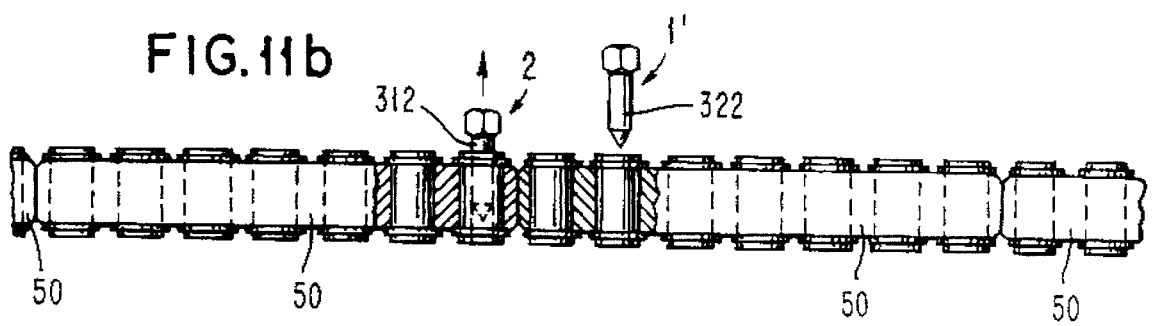
Figure 11C:
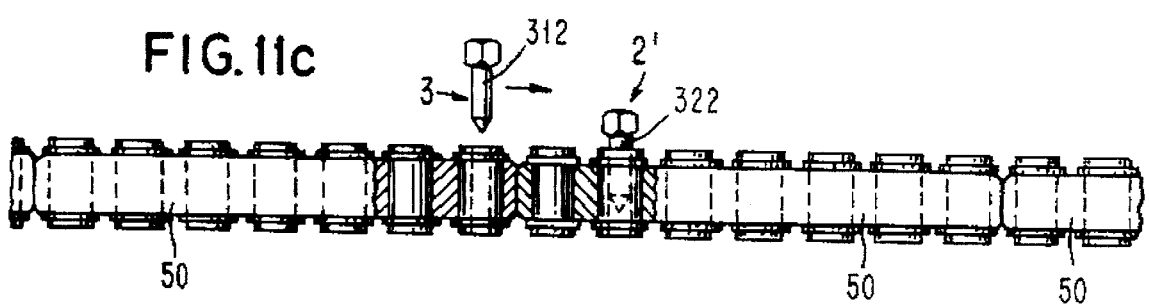
Figure 11D:
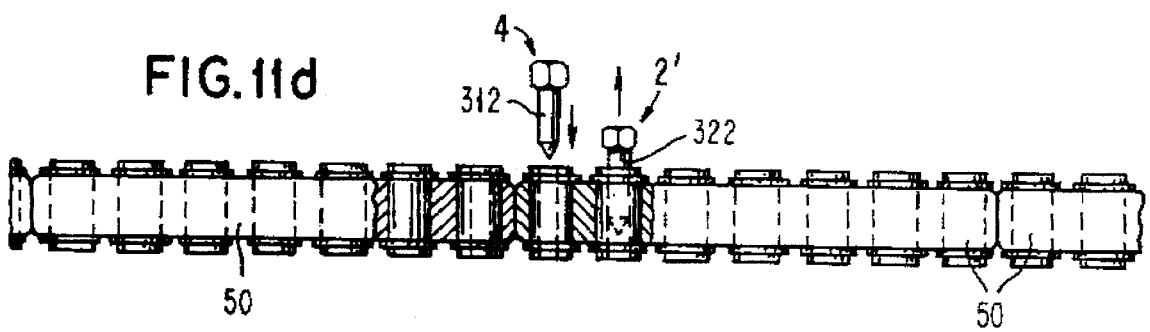
Figure 11E:
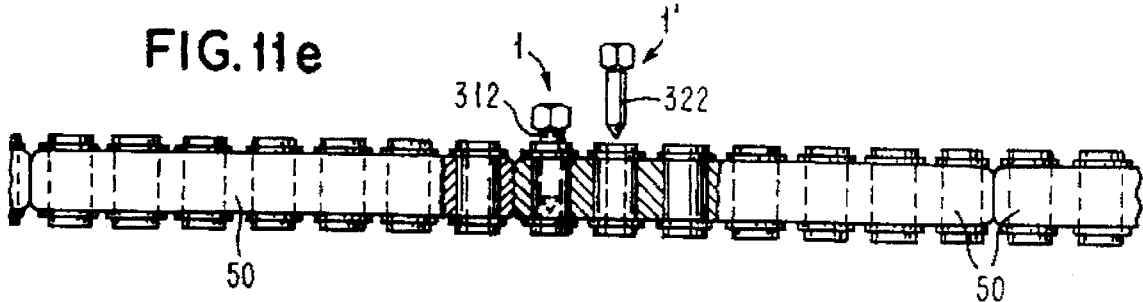

Referring now to FIG. 6, another feature of certain embodiments of the present invention is illustrated. In these embodiments, the vacuum tube 100 will be constructed such that it may be rotated about its longitudinal axis as shown by arrow a in FIG. 6. As understood by those of ordinary skill, such rotation may be accomplished using gear trains, belts and pulleys or other means for transferring rotational motion to a shaft. While rotating, the vacuum tube 100 is also acted upon by a source of vacuum, either the vacuum chamber 60 discussed above, or another source. The product 10 is thus firmly held in place upon the rotating vacuum tube 100 as shown. While the product 10 is rotating, it is brought into contact with a rotating wheel 210 or other application means for applying a coating. Preferably, the rotating wheel 210 provided is shaped and manipulated so as to come into close proximity with a portion of the product 10, such as the central "edge" shown. As the wheel 210 and product 10 rotate, the wheel 210 also passes through a quantity of coating material 222 and precisely coats a portion of the product 10. The wheel 210 rotates about a shaft 202 in the direction shown by arrow b and is mounted on a support structure 200 at an appropriate angle.

The present invention therefore also discloses methods whereby a relatively narrow stripe or band of coating material may be applied to a product. Most preferably, the product and the means for applying the coating rotate and are placed in close proximity. The means for applying the coating is preferably at least partially immersed in a quantity of coating material and passes therethrough while rotating. Using the embodiments illustrated in FIG. 6, it is possible mot only to provide a different color "band" or stripe, but to also increase the thickness of the coating in a specified section, thereby creating the appearance of a seam or an overlapped gelatin capsule.

Referring now to FIG. 9, a novel plate indexing means 300 for incrementally advancing a plurality of product carrier plates 50 through feeder means 80 of the tablet processing system of the present invention can be described. The plate indexing means 300 includes a first engagement means 302 for engaging one or more of the product carrier plates 50 and a first cam means 304 for providing motion in at least two directions to the first engagement means 302. In one direction of movement the first cam means moves the first engagement means 302 from a first position to a second position which thereby advances the product carrier plate 50 an incremental predetermined distance. In the second direction of movement, the first cam means 304 returns the first engagement means 302 to the first position. The first engagement means 302 engages the product carrier plate 50 while moving from the first position to the second position. The plate indexing means 300 incrementally advances the product carrier plates 50 through the feeder means, partially shown at 80, where tablets 10 are dispensed onto the individual holders in the plates 50. In a preferred embodiment of the first cam means, motion in four orthogonal directions to the first engagement means is provided. In this preferred embodiment, the first engagement means is moved into third and fourth positions, out of engagement with the carrier plates 50, for returning the first engagement means from the second position to the first position.

In a preferred embodiment of the plate indexing means 300, a second engagement means 306 is provided for engaging one or more of the plate means 50. The second engagement means 306 is moved between a first position engaging the plate means 50 and a second position out of engagement with the plate means 50. The second engagement means 306 engages the plate means 50 to prevent advancement of the plates 50 during the time when the first engagement means is being returned from its first position to its second position. During this time, the carrier plates 50 must be maintained in position so that the first engagement means will be able to re-engage the plates when it is returned to the first position. Any movement of the plates during the return may result in the plates being unable to be re-engaged causing a shut down of the system. The second engagement means 306 is moved into its second position out of contact with the plates to allow for the controlled advancement of the plates by the first engagement means 302.

Engagement means 302 is comprised of an engagement bar 310 that extends longitudinally over the width of a plurality of plates 50. In the illustrative embodiment shown in FIG. 9, the engagement bar 310 extends over a part or all of six plates. Secured to a bottom surface of engagement bar 310 are a plurality of engagement pins 312. The pins 312 are adapted to fit snuggly into retaining bushings 53 of carrier plates 50. Mounted onto an upper surface of engagement bar 310 is cam means 304. As shown in FIG. 9, cam means 304 is a box cam comprised of a cam follower 314 and a pair of cams 316 positioned in a pair of cam openings 318. As will be more fully explained below, the preferred embodiment of cam means 304 shown in FIG. 9 provides movement to engagement bar 302 in four orthogonal directions in the same plane thereby creating a "box" motion. This "box" motion causes, for every 360° of motion of cams 316, engagement pins 312 to incrementally move from a first position, through second, third and fourth positions, and back to the first position. The "box" motion is provided by the shape of the cams 316 and openings 318. As can be seen in FIG. 9, openings 318 are generally in the shape of a square. Each 90° of motion of cam 316 will cause the cam follower and hence the engagement bar to move in one of the four orthogonal directions. A full 360° of motion therefore provides movement in all four orthogonal directions.

Engagement means 306 is similar to engagement means 302 and therefore comprises an engagement bar 320 having engagement pins 322 secured to a bottom surface thereof. Cam means 308 is mounted to engagement bar 320 and is comprised of a cam follower 324 having a pair of cams 326 positioned in a pair of cam openings 328. In the preferred embodiment shown in FIG. 9, the cams 326 and openings 328 are designed to provide only two directions of motion in the same plane to engagement bar 320. The openings 328 are rectangular in shape as opposed to the square shape of the cam openings 318. In the illustrative embodiment of FIG. 9, the vertical dimension of openings 318 and 328 are identical while the horizontal dimensions of 328 are longer than the horizontal dimensions of openings 318. The size and shape of cams 316 and 326 are identical. However, 180° of motion of cams 326 is required to effect movement to engagement bar 320. For each 180° of motion of cams 326 only one of two directions of motion along the vertical plane will be provided to engagement bar 320. Engagement bar 320 will hence be moved from the position shown in FIG. 9 where the pins 322 are out of engagement with plates 50 and to a second position in which the pins 322 are in engagement with plates 50. While in engagement with plates 50, engagement bar 320 prevents movement of the carrier plates 50 and thereby acts as a locking mechanism. Cam follower 324 also includes opening 330 for receiving a positioning bar 331 shown in FIG. 9*a* that, together with locking wheels 333, prevents movement of engagement bar 320 in the horizontal direction. The wheels 333 are mounted to shafts 337 and rotate with the shafts 337 and move up and down with cam follower 324. As indicated above, the apparatus of the present invention is intended to facilitate coating large numbers of tablets. In the embodiment described above, plates 50 are comprised of seven rows of 33 tablet holders. Thus, the feeder means must be able to dispense a single row of 33 tablets simultaneously onto the carrier plates. It is necessary, therefore, that the plate indexing means ensure that each row of 33 tablet holders is advanced to be in proper registration with the feeder tubes so that all the tablets in the row will be properly seated in the holders. In a preferred embodiment of the present invention, a pair of plate indexing means 300 is provided one on each side of plate 50. As shown in FIG. 8, plates 50 include a row of engagement bushings 53 on each transverse side in order to accomodate engagement pins on each side. A single pair of drive shafts that extends through the cams 316 and 318 of both plate indexing means 300 will provide identical movement to both sides of plates 50. This will ensure that the entire row of holders is accurately advanced to be in registration with the entire row of feeder tubes.

The plate indexing means 300 shown in FIG. 9 acts to incrementally advance the carrier plates in a precisely controlled manner. One important feature is that the apparatus of the invention always maintains the carrier plates under a positive control. This is accomplished through the coordinated movement of the pins 312 and 322 in and out of engagement with the transverse rows of engagement bushings 53 in plates 50. As shown in FIG. 8, there is a single row of engagement bushings 53 on each end. The pins 312 and 322 must therefore engage a single row of bushings 53. In order for this to be accomplished, the engagement bars 310 and 320 must have complementary shapes and cooperate in such a manner in order to enable both sets of pins 312, 322 to be positioned along a single longitudinal axis. Referring now to FIG. 10, a plan view of engagement bars 310 and 320 is shown. As can be seen, the bars 310 and 320 have a tongue and groove like fitting arrangement which allows for each of the sets of pins 312 and 322 to lie along a single longitudinal axis. In addition, the width of the "tongues" 332 is less than the width of the "grooves" 334 of engagement bars 310 and 320 which allows for longitudinal movement of engagement bar 310 with respect to engagement bar 320. For the sake of simplicity, the relative longitudinal movement of engagement bar 310 with respect to engagement bar 320 is shown in phantom only at the pin 312 located on the extreme left hand side of the FIG. 10. Position 1, shown in phantom, is the location of the pins 312 prior to plate advancement. Position 2 is the location of the pins 312 subsequent after plate advancement. Engagement bar 320 does not move in the horizontal plane and therefore pins 322 remain in the positions shown. For a full description of the relative movement of pins 312 and 322, reference to FIG. 11 will be made.

Referring now to FIGS. 11(*a*)–(*e*) there is illustrated the sequential operation of the plate indexing means 300 for incrementally advancing the plates 50. FIG. 11(*a*) shows an engagement pin 312 in position 1 in which the pin is engaged in a plate 50, while at the same time engagement pin 322 is in position 1' out of engagement with a plate 50. Rotation of cams 316 and 326 90° advances the plates 50 the predetermined distance equal to the center-line to center-line distance between each of the transverse rows of product holders in plates 50. As shown in FIG. 11(*b*), pin 312 is advanced in the direction of product flow to position 2 causing each plates 50 to be advanced the predetermined distance. As shown in FIG. 11(*b*), pin 322 remains in position 1', out of engagement with plates 50. As explained above, the first 90° movement of cam 326 does not result in cam 326 contacting cam follower 324 so that no movement will occur to engagement bar 320. As shown in FIG. 11(*c*), upon a second 90° rotation of cams 316 and 326, pin 312 is moved out of engagement with plates 50 to position 3. The second 90° movement of cam 326 causes movement of engagement bar 320 which moves pin 322 downward to position 2' engaging plates 50. Next, as shown in FIG. 11(*d*) the third 90° rotation of cams 316 and 326 results in pins 312 moving in the opposite direction of product flow to position 4. During this 90° rotation of cam 326, no movement is effected to engagement bar 320 and thus pins 322 remain in position 2' engaged with plates 50. As noted previously, a positioning bar is in contact with cam follower 324 and is connected to the frame assembly of the processing apparatus to prevent longitudinal movement of the engagement bar 320. Thus, by maintaining pins 322 in engagement with plates 50 during the time when pins 312 are out of engagement with plates 50, assures that the plates 50 are always under positive control. As shown in FIG. 11(*e*), the fourth 90° rotation of cams 316 and 326 results in pin 312 moving downward to position 1 re-engaging plate 50. The fourth 90° rotation of cam 326 results in movement of engagement bar 320 upward moving pins 322 back up to position 1' out of engagement with plates 50.

As noted above, the relative shape of cams 316, 326 and cam opening 318, 328 provide the complementary movement of engagement bars 310 and 320. Referring back to FIG. 9, the first box cam 304 includes an eccentric cam 316 rotatable 360° in the cam follower housing 314, each 90° of rotation, providing a predetermined motion time period and a predetermined dwell time period for the engagement bar 310. In the illustrative embodiment shown in FIG. 9, each 90° of rotation of cam 316 provides a motion period for approximately 72° of that rotation and a dwell time for approximately 18° of that rotation to move engagement bar 310 in each of the four directions. Likewise, cam 326 is an eccentric cam rotatable 360° that provides for each 180° of rotation a predetermined motion time period and a predetermined dwell time period for the engagement bar 320. In the illustrative embodiment shown in FIG. 9, each 180° of rotation of cam 326 provides a motion time period for about 72° of that rotation and a dwell time period for about 108° of that rotation to move engagement bar 320 in each of two directions.

Plate indexing means 300 as described above, provides precise incremental advancement of the plates 50 through the feeder means to provide accurate feeding and loading of tablets onto the carrier plates. High precision in the loading of the tablets onto the plates is necessary to allow the system to accurately coat the product with the various coating arrangements as desired. Conventional drive components including motors, drive shafts and the like are required to provide the rotation to cams 316 and 326, all of which are well known to those skilled in the art and hence there is no need to provide details of these elements.

Referring now to FIGS. 1 and 12, the feeder means 80 includes hopper 82 and a plurality of feeder tubes 84. Feeder means 80 also preferably includes separation means 86 for eliminating broken tablets so that only full sized tablets are introduced into the hopper 82. Feeder means 80 further includes dispensing means 88 for orienting and depositing one or more products onto the product carrier plates 50. The separation means 86 includes a perforated plate 81, shown in FIG. 13, that is caused to vibrate by a vibrator means 83. A plastic tote or other container 85 containing a supply of product to be coated is attached to a chute 87. As shown in FIG. 12, tablets 10 in tote 85 are allowed to feed into the chute 87 causing the product to travel into a angled chute 89. The tablets 10 are transferred through chute 89 in essentially a single layer to perforated plate 81. The perforated plate 81 and chute 89 are attached to the vibrator 83 and are positioned at an angle whereby vibrations cause the tablets to "walk" across the perforated plate and fall into chute 91. Perforated plate 81 is comprised of a series of holes 93 which are sized just slightly smaller than the diameter of the tablets to be coated. As the product walks across the perforated plate, partial or broken tablets will fall through the holes 93 while full sized tablets will pass completely across the plate and fall into chute 91. A bin 95 is positioned below the perforated plate 81 to collect the broken pieces.

Chute 91 transfers the full tablets 10 to hopper 82 of feeder means 80. Reciprocating drive means 90 causes hopper 82 to move in an up and down motion resulting in tablets 10 entering feeder tubes 84. The dispensing means 88 orients and dispenses the tablets 10 onto the plate means 50. The dispensing means 88 fills a plate 50 one row at a time. In a preferred embodiment of the present invention, feeder tubes 84 contain a linearly disposed plurality of product 10 to be deposited. It will be understood that FIG. 12 is a side view, partially cross-sectioned, therefore only one "column" of product is visible. However, in a preferred embodiment, a column of product 10 is positioned over each product holder across an empty row of plate 50. In the preferred embodiment shown in FIGS. 9 and 12, the dispensing means includes a parallel linkage 91. The parallel linkage 91 causes product 10 to be fed in a single row and correctly positioned over a row of open product holders 31. Product control stops 92, 93 are positioned to extend radially into and out of the feeder tube 84. Stop control bars 94 and 96 are attached to each product control stop 92, 93. In turn, the control bars 94, 96 are connected by parallel links 97, 98. As shown in FIG. 10, the parallel linkage 91 is connected to engagement bar 310 through a transfer motion means 99. In operation, as shown in FIGS. 9, 10 and 12, when engagement bar 310 moves in a direction opposite to that of product flow shown by the arrow, the motion transferred via the links 97 and 98 causes stop control bar 92 to come in contact with a tablet 10 holding that tablet in place preventing all tablets above that tablet to fall any further through the tube 84. At the same time, stop control bar 93 is withdrawn from the tube allowing a single product to fall through the tube for placement onto the carrier plate 50. Upon the motion of engagement bar 310 in the direction of product flow, motion will be transferred via links 97 and 98 to stop control bars 92 and 93 to cause control bar 93 to be reinserted into the feeder tube 84 and to release stop control bar 92 from the tubes in order to allow products 10 to drop to a position shown in FIGS. 9 and 12. It is during movement of engagement bar 310 in the direction of product flow that the tablet 10 previously released by linkage 91 is oriented and dispensed onto a product holder 30.

Figure 14A:
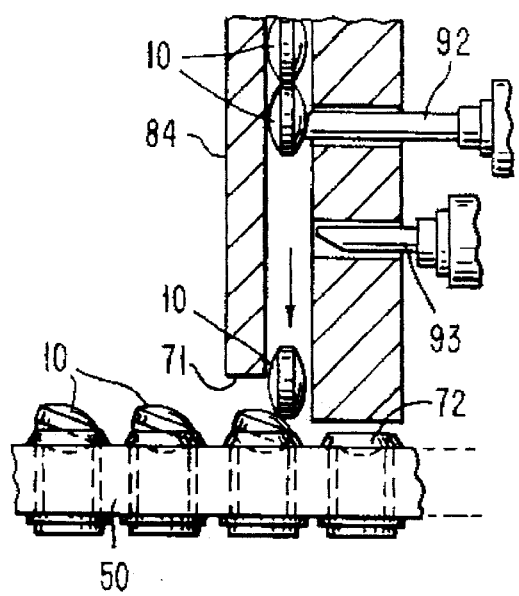
FIGS. 14a and 14b are cross-sectional views of the passive means for dispensing tablets onto a product holder.
Figure 14B:
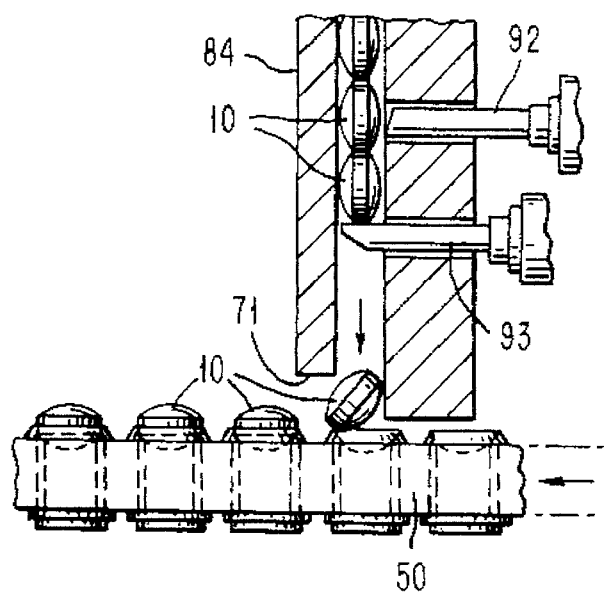

A more detailed view of the actual orienting and dispensing of product 10 onto the product holders is shown in FIGS. 14a and 14b. The means for depositing and orienting a tablet 10 onto an open product holder 30 in the illustrative embodiment of FIGS. 14a and 14b is a passive "knock over" mechanism. As shown, one side of the feeder tube, the side downstream of product flow, is provided with an opening 71. The remaining portion of the feeder tubes 84 extend to a position nearly touching the top of product holders 30 as shown at 72. When engagment bar 310 is moved in a direction opposite to that of product flow causing a tablet 10 to fall all the way to the bottom of feeder tube 84, the position of the product carrier 50 is such that the tablet falls onto the previously deposited tablet. The resulting position of the first released tablet is shown in FIG. 14a. Preferably, the product carrier plate 50 is positioned in relation to the feeder tubes 84 slightly off center so that the falling tablet 10 falls on a surface of the previously deposited tablet between the center of the tablet and the end of the tablet. This arrangement is preferred as compared to allowing the tablets 10 to fall directly onto an open product holder as it has been found that severe bouncing occurs when tablets fall directly onto the holders sometimes causing disorientation or damage to the tablets. By having the tablet fall onto another tablet, the bouncing is reduced. As the engagement bar moves in the direction of product flow, the top half of tablet 10, engages the bottom edge of the opening 71 and the lower half of the tablet 10 is caused to rotate through the opening, thereby orienting the tablet with its greater diameter horizontally positioned and causing the tablet to land in that orientation onto the next open product holder as shown in FIG. 14b.

Figure 15:
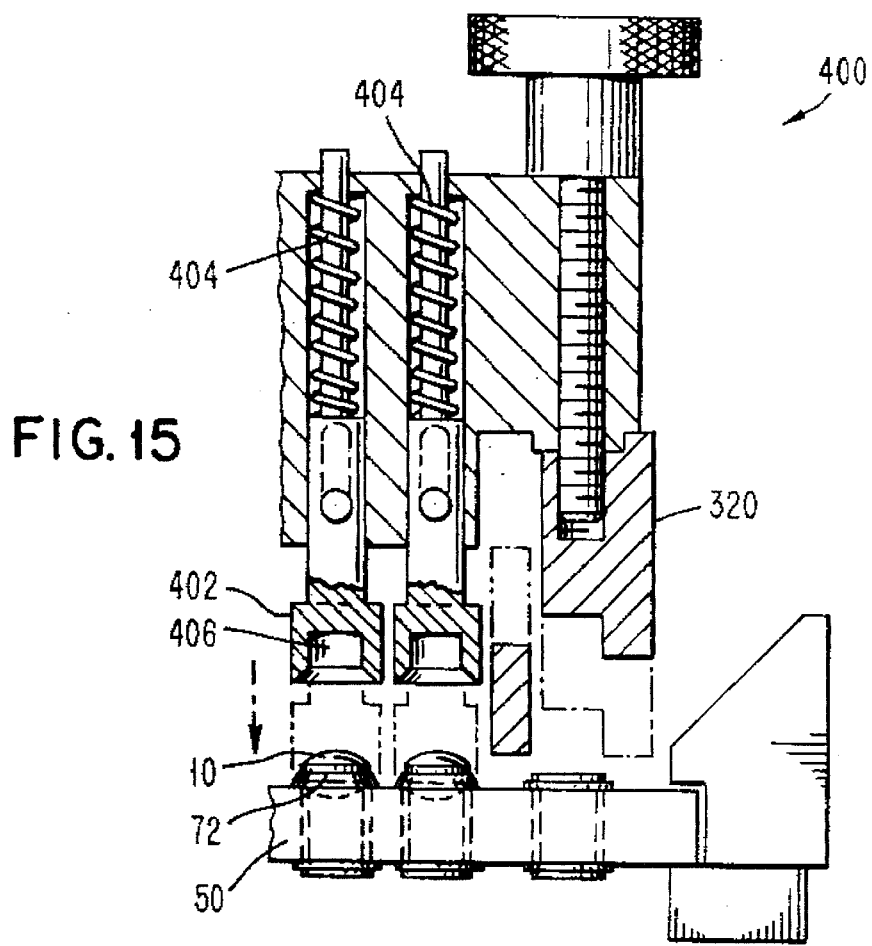
FIG. 15 is a cross-sectional view of the setting means of the present invention.

In a preferred embodiment of the present invention, the feeder means 80 is also provided with a tablet setting means 400 downstream of the feeder tubes in the direction of the product flow for properly seating the tablets in individual product holders after being dispensed from the feeder tubes. The product setting means 400 can be seen in FIGS. 9 and 10 and is shown in a detailed cross-sectional view in FIG. 15. Setting means 400 includes a setting head 402 connected to a reciprocating arm means 404 for moving the setting head from a first position out of contact with tablets 10 to a second position shown in phantom in FIG. 15 in which the head 402 contacts tablet 10. The head includes an opening 406 shaped to be complementary to the shape of the product being set. An actuating means is provided to control the reciprocating motion of the setting means. In the embodiment shown in FIG. 15, the setting means 404 is connected to engagement bar 320 which reciprocates up and down to selectively engage pins 322. In this embodiment, the setting means 400 is moved into a position to contact the tablets each time the engagement bar is caused to move into the position where pins 322 are engaged in the product holders 31. As shown in FIGS. 10 and 15, a row of setting means 400 is provided so that a row of products may be seated at a time.

Figure 16:
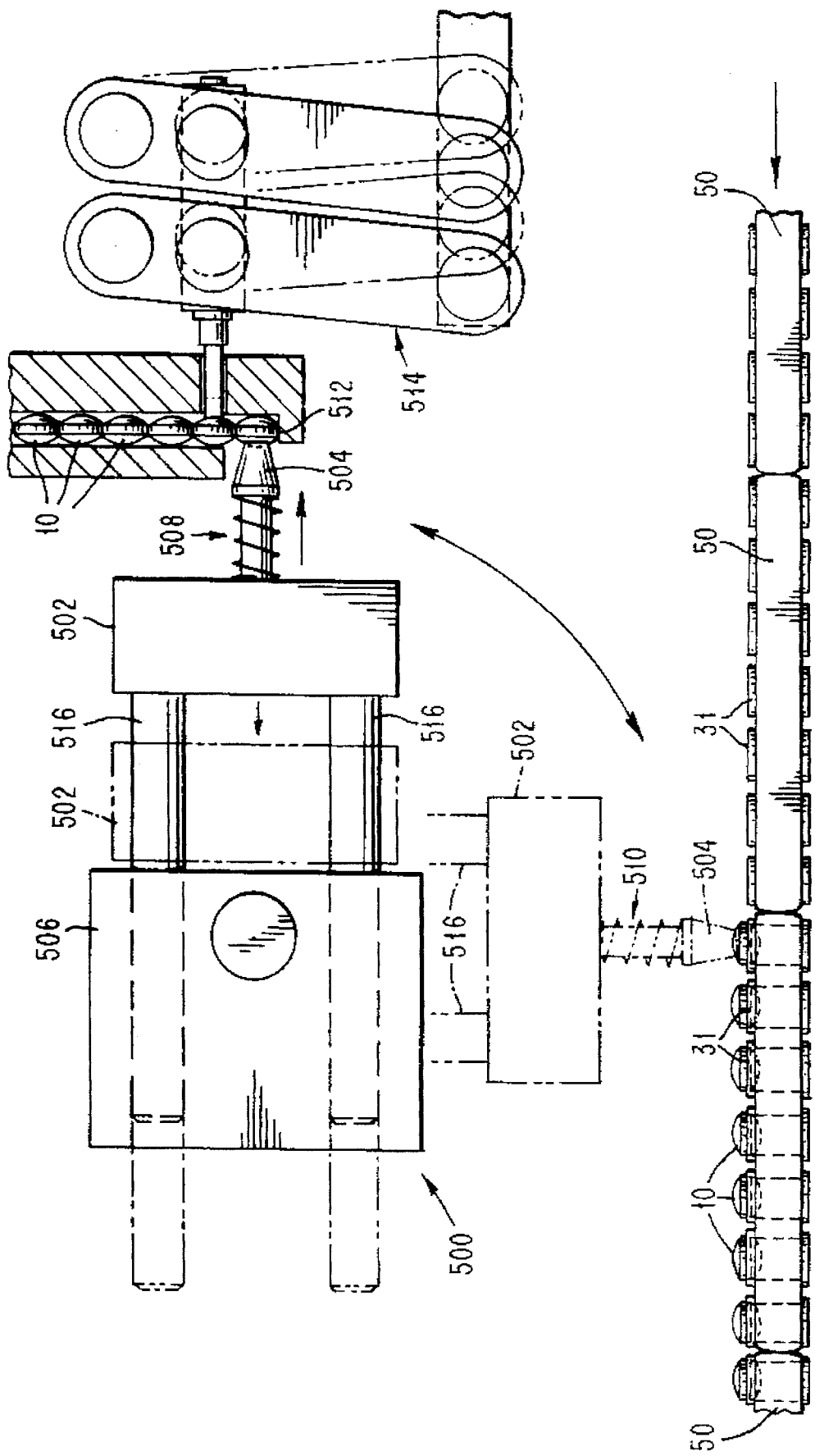
FIG. 16 is a cross-sectional view of one embodiment of a vacuum pick-up device of the product dispensing means of the present invention.

In an alternative embodiment of the present invention as shown in FIG. 16, the dispensing means is comprised of a transfer means for capturing products from the feeder tubes and disposing the product in the holding fixtures or carrier plate means. In this embodiment, the dispensing means comprises a vacuum means 500 which includes a vacuum chamber 502 connected to a vacuum source for delivering a vacuum to a plurality of pick-up heads 504. An actuating means 506 is provided for positioning the vacuum pick-up heads from a first position shown at 508 for capturing products in the feeder tubes and for positioning the captured product at a second position shown at 510 for releasing the product onto the holding means. In this embodiment, the feeder tube guide means includes a seat 512 which acts as a capture seat means for retaining a single product to be transferred. A parallel linkage 514 may optionally be provided with a product control stop 516 which urges against a tablet immediately above the tablet located in the capture seat 512. The linkage 514 results in the elimination of any force from the column of tablets on the tablet being captured that may interfere with the capture process. Alternatively, a pair of product stop bars similar to that shown in FIG. 12 may be employed. In operation, the actuating means 506 rotates the vacuum heads to the first position 508 and an extension means 516 extends the vacuum chamber 502 and the vacuum heads 504 so that the heads contact the tablets in the capture seat. The vacuum is actuated causing the tablets to be held by the vacuum heads 504. The heads 504 are then retracted removing the tablets from the seat. The retracted heads 504 with the captured tablets are then rotated to the second position where the heads 504 are again extended causing the tablets to be positioned on an empty row of product holders 31. The vacuum is released and the vacuum heads 504 retracted resulting in the tablet being deposited on the product holders.

As shown in FIG. 17, the product pick-up means 504 is comprised of an outer pick-up shell 522 having tips 524 shaped complementary to the product being captured and deposited. A vacuum tube 526 is positioned within shell 522 and may itself be extended and retracted within the shell for increasing or decreasing the vacuum force applied to the product.

As shown in FIG. 17, a product setting means 520 may also be provided with the vacuum feeder means 500. The setting means 520 is attached to the vacuum chamber 502 and is rotated throughout the various positions and is extended and retracted at the same time the vacuum pick-up heads 504 are extended and retracted. Thus, when the vacuum heads 504 are extended to deposit a tablet onto a tablet holder the setting head 520 is extended to properly seat the tablets in one or more rows downstream of the tablets being deposited.

Although certain embodiments of the methods and apparatus of the present invention have been described above with particularity, these examples are for purposes of illustration and are not limiting. Numerous variations and adaptations of the principles of the present invention will immediately present themselves to those of ordinary skill. Accordingly, reference should be made to the appended claims to ascertain the scope of the present invention.

What is claimed is:

1. Apparatus for incrementally advancing a plurality of product carrier plate means having at least one product holder through a feeder means of a product processing system, said apparatus comprising:

first engagement means for engaging one or more of said product carrier plate means at a location remote from said product holder;

first cam means providing motion in at least two directions to said first engagement means for moving said first engagement means from a first position to a second position to advance said product carrier plate means a predetermined distance in the direction of product flow, and for returning said first engagement means to said first position, said first engagement means being in engagement with said product carrier plate means while in said first and second positions;

second engagement means for engaging one or more of said product carrier plate means; and second cam means providing motion in two directions for moving said second engagement means between a first position engaging said product carrier plate means to prevent advancement thereof and a second position out of engagement with said product carrier plate means to allow advancement thereof.

2. The apparatus of claim 1 wherein said first cam means is a box cam providing motion in four directions for moving said first engagement means to third and fourth positions in returning said first engagement means to said first position, said first engagement means being out of engagement with said product carrier plate means in said third and fourth positions.

3. The apparatus of claim 1 wherein said first engagement means includes one or more pins attached to a first engagement bar, said one or more pins engaging one or more holes disposed upon opposed side edges of said product carrier plate means when said first engagement means is moved into the first position.

4. The apparatus of claim 1 wherein said product carrier plate means comprises transverse rows of individual product holders and a plate adapted to retain said individual product holders.

5. The apparatus of claim 4 wherein first said cam means includes means for incrementally advancing said product carrier plate means a distance equal to the center to center distance between said transverse rows of individual product holders.

6. The apparatus of claim 4 wherein said individual product holders comprise resilient finger means for retaining said holders in the product carrier plate means.

7. The apparatus of claim 6 where said resilient finger means comprise a substantially cylindrical portion having first and second ends and two or more longitudinal slots defining said resilient finger means.

8. The apparatus of claim 7 where said individual product holders include a shoulder portion on said first end and a tapered flange on said second end.

9. The apparatus of claim 1 wherein said second engagement means includes one or more pins attached to a second engagement bar, said one or more pins engaging one or more holes disposed upon opposed side edges of said product carrier plate means when said second engagement means is moved into said first position.

10. The apparatus of claim 2 wherein said box cam comprises an eccentric cam rotatable 360° in a housing, each 90° of rotation providing a predetermined motion time period and a predetermined dwell time period for said first engagement means.

11. The apparatus of claim 10 wherein said eccentric cam and housing, provides, for each 90° of rotation, the motion period for about 72° of rotation and the dwell time period for about 18° of rotation.

12. The apparatus of claim 1 wherein said second cam mean comprises an eccentric cam rotatable 360° in a housing, each 180° of rotation providing a predetermined motion time period and a predetermined dwell time period for said second engagement means.

13. The apparatus of claim 12 wherein said eccentric cam and housing provide, for each 180° of rotation, the motion time period for about 72° of rotation and the dwell time period for about 108° of rotation.

14. The apparatus of claim 1 wherein each of said first and second cam means comprises a pair of eccentric cam devices.

15. The apparatus of claim 14 wherein said pair of eccentric cam devices for said second engagement means includes bar means for preventing movement of said carrier plate means longitudinally in the direction of product flow.

16. The apparatus of claim 1 wherein said feeder means comprises dispensing means for orienting and depositing one or more products onto said product carrier plate means, said apparatus further including means connecting said dispensing means to said first cam means whereby said product is dispensed in conjunction with one or more movements of said first engagement means.

17. The apparatus of claim 16 wherein said feeder means includes one or more feeder tubes which retain a plurality of products in a longitudinally aligned orientation.

18. The apparatus of claim 17 wherein said product carrier plate means comprises one or more transverse rows of individual product holders.

19. The apparatus of claim 18 where said dispensing means includes parallel linkage means connected to said first cam means which feeds and positions a product in said tubes to a position proximate to each of said individual product holders of a row of said holders.

20. The apparatus of claim 19 wherein said parallel linkage means are connected to one or more product control stops and one or more stop control bars which cooperate to allow a single product to be positioned proximate to each of said individual product holders of a row of said holders.

21. The apparatus of claim 20 wherein said parallel linkage means is connected to said first cam means such that said single product will be proximately positioned upon the return movement of said first engagement means.

22. The apparatus of claim 1 wherein said feeder means comprises dispensing means for orienting and depositing one or more products onto said product carrier plate means, said apparatus further including means connecting said dispensing means to said first cam means whereby said product is dispensed in conjunction with one or more movements of said first engagement means.

23. The apparatus of claim 22 wherein said feeder means further comprises product setting means connected to said second cam means for properly seating said product in individual product holders in said product carrier plate means.

24. The apparatus of claim 23 wherein said setting means includes a setting head connected to a reciprocating arm means for moving the setting head to contact and properly seat the product in said individual product holders and for moving the setting head out of contact with the product.

25. The apparatus of claim 17 wherein said feeder means includes a hopper means for containing a plurality of product, and further including selection means, cooperating with said hopper means, for eliminating partial pieces of said product before said product is disposed into said feeder tubes.

26. The apparatus of claim 25 wherein hopper means includes vibratory means for agitating said product.

27. The apparatus of claim 26 wherein said selection means comprises a perforated plate having a plurality of holes with a diameter a predetermined amount smaller than the diameter of said products for retaining said products and for allowing partial pieces of said products to fall through said holes in response to said vibratory means.

28. The apparatus of claim 27 wherein said selection means further includes an elimination chute for disposing of said partial pieces.

29. The apparatus of claim 28 wherein said hopper means further includes delivery means for transferring said properly sized products retained by said perforated plate to said feeder tubes.

30. A method for incrementally advancing a plurality of product carrier plate means through a feeder means of a product processing system, said method comprising the steps of:

providing a first engagement means for engaging one or more of said product carrier plate means having a plurality of product holders secured therein at a location remote from said product holders;

moving said first engagement means from a first position to a second position to advance said product carrier plate means a predetermined incremental distance in the direction of product flow;

returning said first engagement means to said first position without moving said product carrier plate means by moving said first engagement means to third and fourth positions out of engagement with said product carrier plate means;

repetitively moving said first engagement means from said first position to said second position and returning to said first position to repetitively cause one or more product holders in said carrier plate means to be in registration with one or more feeder tubes of said feeder means;

providing a second engagement means for engaging one or more of said product carrier product means;

moving said second engagement means to a first position in engagement with said product carrier plate means when said first engagement means is in said third and fourth positions to prevent advancement of said carrier plate means;

moving said second engagement means to a second position out of engagement with said product carrier plate means when said first engagement means is in its first and second position to allow advancement of said carrier plates;

repetitively moving said second engagement means between its first and second positions in cooperation with the repetitive movement of said first engagement means; and placing one or more products onto said one or more product holders when said holders are in registration with said feeder tubes.

31. The method of claim 30 wherein said first engagement means is moved in four orthogonal directions when moved from the first position to the second, third and fourth positions and returned to the first position.

32. The method of claim 30 where the movement of said first engagement means from said first position to said second position incrementally advances one or more product holders containing a product to be in registration with a product setting means, and said method further including the step of actuating said product setting means.

33. The method of claim 32 wherein said setting means is actuated when said second engagement means is in its second position.

* * * * *